US009754079B2

United States Patent
Knight et al.

(10) Patent No.: US 9,754,079 B2
(45) Date of Patent: Sep. 5, 2017

(54) ADVANCED SYSTEM AND METHOD FOR OXYGEN SATURATION MONITORING

(75) Inventors: Adrian Knight, Shawnee, KS (US); Dana Voien, Laguna Niguel, CA (US)

(73) Assignee: SleepSafe Drivers, Inc., Laguna Niguel, CA (US)

(*) Notice: Subject to any disclaimer, the term of this patent is extended or adjusted under 35 U.S.C. 154(b) by 1627 days.

(21) Appl. No.: 13/328,995

(22) Filed: Dec. 16, 2011

(65) Prior Publication Data

US 2012/0165630 A1    Jun. 28, 2012

Related U.S. Application Data

(63) Continuation-in-part of application No. 12/928,903, filed on Dec. 22, 2010, now Pat. No. 8,771,185.

(51) Int. Cl.
| | |
|---|---|
| *A61B 5/00* | (2006.01) |
| *G06F 19/00* | (2011.01) |
| *A61B 5/1455* | (2006.01) |
| *A61B 5/0205* | (2006.01) |
| *A61B 5/087* | (2006.01) |
| *A61B 5/113* | (2006.01) |
| *A61B 5/02* | (2006.01) |
| *G09F 3/03* | (2006.01) |

(52) U.S. Cl.
CPC ...... *G06F 19/3418* (2013.01); *A61B 5/14551* (2013.01); *A61B 5/6826* (2013.01); *A61B 5/6831* (2013.01); *A61B 5/02* (2013.01); *A61B 5/0205* (2013.01); *A61B 5/087* (2013.01); *A61B 5/1135* (2013.01); *A61B 2562/08* (2013.01); *G09F 3/03* (2013.01)

(58) Field of Classification Search
None
See application file for complete search history.

(56) References Cited

U.S. PATENT DOCUMENTS

| | | | | |
|---|---|---|---|---|
| 3,698,383 | A * | 10/1972 | Baucom | A61B 5/117 283/67 |
| 4,121,360 | A * | 10/1978 | Vlerebome | G09F 3/005 40/586 |
| 5,452,930 | A | 9/1995 | Morgan | |

(Continued)

OTHER PUBLICATIONS

Powell et al., "The Road to Danger—The Comparative Risks of Driving While Sleepy" Laryngoscope 111: May 2001.

(Continued)

*Primary Examiner* — William Thomson
*Assistant Examiner* — Marie Archer
(74) *Attorney, Agent, or Firm* — Mintz Levin Cohn Ferris Glovsky and Popeo, P.C.

(57) ABSTRACT

A method that includes configuring a first and a second identification band with unique serial numbers, each of said bands being connected to a signal cable attached to a sensor is provided. The first identification band is securely fixed to a first location on the patient and the second identification band is securely fixed to a second location on the patient. The first and second identification bands are connected with a bridging band. The signal cable is connected to a diagnostic test monitoring system and the patient's oxygen saturation is monitored. The first and second identification bands are configured to evidence tampering when removed.

8 Claims, 24 Drawing Sheets

(56) References Cited

U.S. PATENT DOCUMENTS

| | | | |
|---|---|---|---|
| 5,631,446 A * | 5/1997 | Quan | H01R 12/62 174/254 |
| 5,904,646 A * | 5/1999 | Jarvik | A61M 39/0247 600/16 |
| 6,220,876 B1 * | 4/2001 | Avila | H01R 9/2466 439/34 |
| 6,241,684 B1 * | 6/2001 | Amano et al. | 600/531 |
| 6,588,812 B1 | 7/2003 | Garcia et al. | |
| 6,915,802 B1 | 7/2005 | Anderson et al. | |
| 7,168,626 B2 * | 1/2007 | Lerch | G06K 19/07381 235/380 |
| 7,423,526 B2 | 9/2008 | Despotis | |
| 7,481,370 B2 * | 1/2009 | Davis | A61B 5/117 235/375 |
| 7,849,619 B2 | 12/2010 | Mosher, Jr. et al. | |
| 8,225,540 B2 * | 7/2012 | Shigaraki | A61B 19/44 40/633 |
| 8,308,640 B2 | 11/2012 | Baldus et al. | |
| 8,410,926 B1 | 4/2013 | Gary, Jr. et al. | |
| 8,474,584 B2 | 7/2013 | Mrocki et al. | |
| 8,679,012 B1 | 3/2014 | Kayyali | |
| 2002/0115919 A1 | 8/2002 | Al-Ali | |
| 2003/0040785 A1 * | 2/2003 | Maschino | A61N 1/0556 607/118 |
| 2003/0173408 A1 * | 9/2003 | Mosher et al. | 235/492 |
| 2004/0025866 A1 | 2/2004 | Vedrine et al. | |
| 2004/0060215 A1 * | 4/2004 | Riley | B42D 15/00 40/633 |
| 2004/0068906 A1 * | 4/2004 | Riley | B42D 15/00 40/633 |
| 2004/0084047 A1 | 5/2004 | Hickle | |
| 2004/0138535 A1 | 7/2004 | Ogilvie | |
| 2004/0236199 A1 | 11/2004 | Hawthorne et al. | |
| 2004/0260154 A1 | 12/2004 | Sidelnik et al. | |
| 2005/0125363 A1 | 6/2005 | Wilson et al. | |
| 2006/0005441 A1 * | 1/2006 | Riley et al. | 40/633 |
| 2006/0011415 A1 * | 1/2006 | Fischer | A62B 1/14 182/7 |
| 2006/0225332 A1 | 10/2006 | Zenisek | |
| 2007/0015728 A1 | 1/2007 | Ford | |
| 2007/0017136 A1 | 1/2007 | Mosher et al. | |
| 2007/0073116 A1 * | 3/2007 | Kiani | A61B 5/14552 600/310 |
| 2007/0118028 A1 * | 5/2007 | Kitajima | A61B 5/11 600/310 |
| 2007/0124973 A1 * | 6/2007 | Stallings | G09F 3/005 40/633 |
| 2007/0199567 A1 | 8/2007 | Kanzer | |
| 2008/0041379 A1 | 2/2008 | Turiello | |
| 2008/0076995 A1 | 3/2008 | Hoarau | |
| 2008/0221402 A1 | 9/2008 | Despotis | |
| 2008/0257673 A1 | 10/2008 | Mrocki et al. | |
| 2009/0212957 A1 | 8/2009 | Burris | |
| 2010/0024268 A1 * | 2/2010 | Landsman | G09F 3/005 40/633 |
| 2010/0056886 A1 | 3/2010 | Hurtubise et al. | |
| 2010/0231378 A1 * | 9/2010 | Ward | 340/539.11 |
| 2010/0312075 A1 | 12/2010 | McGonigle et al. | |
| 2010/0327063 A1 * | 12/2010 | Medina | A61B 5/14552 235/454 |
| 2011/0115221 A1 | 5/2011 | Kaplan | |
| 2011/0213255 A1 | 9/2011 | Finburgh et al. | |
| 2011/0224564 A1 * | 9/2011 | Moon et al. | 600/509 |
| 2012/0036753 A1 * | 2/2012 | Landsman | A44C 5/0015 40/633 |
| 2012/0071741 A1 * | 3/2012 | Moussavi | A61B 5/4818 600/340 |
| 2012/0108983 A1 | 5/2012 | Banet et al. | |
| 2012/0190949 A1 | 7/2012 | McCombie et al. | |

OTHER PUBLICATIONS

DOT/FMCSA, Medical Review Board's Recommendations of Jan. 2008.

Hartenbaum, Natalie, "The DOT Medical Examination: A Guide to Commercial Drivers' Medical Certification" Nov. 8, 2011.

Peaco, Ed, "Truckers scrutinized for sleep apnea," Nov. 14, 2011.

Nunlist, Tom and Oliver B. Patton, "A better Way to Drug Test? Hair Testing Reveals Disturbing Facts About Driver Drug Use and DOT Requirements," Nov. 21, 2011.

Hartenbaum, Natalie, "Transportation and Obstructive Sleep Anea Health, Saftey & Productivity Risks" Nov. 11, 2011.

Transcription of US National Transportation Safety Board hearing, in the matter of: "Public Forum on Truck and Bus safety: A Decade of Progress," May 11, 2011.

WikiHow Article, "How to Pass a Drug Test". Retrieved from the internet on Mar. 13, 2012.

Sharwood, Lisa N. et al., "Assessing Sleepiness and Sleep Disorders in Australian Long-Distance Commercial Vehicle Drivers: Self-Report Versus an "At Home" Monitoring Device," Sleep, vol. 35, No. 4, pp. 469-475, 2012.

"WatchPAT Complete Overview." Itamar Medical. Apr. 18, 2012. Web. Mar. 8, 2016. Relevant pp. 1-2. Wayback Machine. <https://web.archive.org/web/20120418180253/http://www.itamar-medical.com/WatchPAT/Patient/WatchPAT/Complete_Overview.html>.

PCT International Search Report and Written Opinion dated Jun. 21, 2012, for PCT application No. PCT/US2012/065646.

Extended European Search Report dated Feb. 17, 2017 for European Patent Application No. 11852192.1-1502, dated Feb. 24, 2017 (Feb. 24, 2017).

* cited by examiner

ADVANCED SYSTEM AND METHOD FOR OXYGEN SATURATION MONITORING

CROSS REFERENCE TO RELATED APPLICATIONS

This application is a continuation in part of U.S. patent application Ser. No. 12/928,903, titled, "System and Method for Reliable Sleep Diagnostic Testing," filed Dec. 22, 2010, which, along with any applications it claims priority to (if any), are incorporated by reference in their entirety herein.

BACKGROUND OF THE INVENTION

Field of the Invention

The present invention relates generally to portable/unattended sleep study monitoring, recording, and overnight oximetery testing, and more specifically to securing a sensor (such as an oximetry/oxygen saturation sensor) to an individual for purposes of conducting a sleep study with test fraud mitigation by virtue of preventing "test switching" between patients.

Description of the Related Art

Sleep apnea is a disorder affecting many individuals, and the disorder can have various adverse consequences, including death in the most extreme circumstances. One area where sleep apnea is of particular concern is when persons are performing "risk sensitive" job activities, such as operating dangerous machinery, driving vehicles on public roads, public transportation, security, military and medical jobs, and mining and oil work.

A driver impairment study directed by Doctor's Nelson Powell and Robert Riley was conducted at the General Motors proving grounds. The study results were published in Laryngoscope 111: May 2001, in a paper titled—'The Road to Danger—The Comparative Risks of Driving While Sleepy'. The Powell and Riley study revealed that eleven measured reaction time metrics for various individuals showed that sleepy drivers were the same as the alcohol-challenged drivers when operating a car and attempting to avoid obstacles. These results are widely accepted as suggesting that driving while sleepy should be recognized as potentially dangerous or as at least as dangerous as driving while under the influence of alcohol.

In view of dangers of driving while sleepy or fatigued and an understanding of the effects of obstructive sleep apnea, the Department of Transportation continues to modify requirements for a commercial vehicle driver (or pilot, ship captain or rail operator) to be deemed "Fit for Duty." The DOT/FMCSA released their Medical Review Board's Recommendations of January 2008, where the Sleep Apnea Guidelines include monitoring drivers for symptoms and potential diagnosis for sleep apnea.

Sleep apnea testing, screening, and monitoring requirements have created an environment where individuals wishing to obtain or keep a commercial drivers license (or any other "fit for duty status") are fearful of testing positive for sleep apnea, failing to achieve compliant usage, and thus having their license refused or revoked. The fear of losing a job has led some drivers to introduce fraud during ambulatory sleep apnea monitoring. For example, the individual being monitored may switch their oxygen saturation-monitoring device to another person who may be known to present an acceptable oxygen saturation level. The person believed to have acceptable levels wears the device during his or her sleep period, thereby providing a false negative indication for apnea in the desired test subject.

Current methods and designs may become problematic during ambulatory studies when the test individual is not under direct supervision. Ambulatory (e.g., portable), sleep apnea tests can be hours in duration and are typically set up in locations such as, but not limited to, a sleep lab, test subject's home, truck cab, or a hotel. Signals are recorded while the patient is asleep. Prior to or during the testing stage of the oxygen saturation monitoring procedure, the patient being studied may remove the sensing device and give the device to another individual believed to have satisfactory saturation levels. Also, current designs may fail to properly exhibit evidence of tampering when an individual attempts to remove the testing device and associated apparatuses.

With in-patient polysomnography sleep lab supervised tests, fraud may occur by simply having another individual take the desired individual's test by presenting a fake identification such as a non-commercial driving license. Many of today's labs currently operate without checking the patient's identification and presume the person present is the person referred for the test.

Based on the foregoing, it would be beneficial to offer a method for safely and securely conducting an ambulatory sleep apnea test, where the sensing device is secured to the test individual in a tamper resistant or tamper evident manner.

SUMMARY OF THE INVENTION

In view of the foregoing, there is a need for methods and apparatus to test a patient for a sleep disorder in which the tampering with the testing mechanism is detectable or precluded.

Provided in some embodiments is a method for oxygen saturation monitoring that includes: configuring a first and a second identification band with unique serial numbers, each of said bands being connected to a signal cable that includes a sensor; securely fixing the first identification band to a first location on the patient and the second identification band to a second location on the patient; connecting the first and second identification bands with a bridging band; connecting the signal cable to a diagnostic test monitoring system; and monitoring the oxygen saturation of the patient through the sensor, in which the first and second identification bands are configured to evidence tampering when removed.

In some embodiments, a method of diagnostic testing a patient is provided that includes attaching a sensor with a sensor signal cable to a patient, configuring an identification band in a secure arrangement, in which the secure arrangement secures the sensor and the sensor signal cable to the patient, and connecting the sensor signal cable to a diagnostic test monitoring system for purposes of conducting a diagnostic test, in which the identification band is configured to evidence tampering when removed.

Provided in some embodiments is a method for securely affixing a sensor to a patient that includes: attaching the sensor to a finger of a patient with a sensor signal cable routed along a hand of the patient; configuring an identification band to encircle the signal cable and a wrist of the patient using a secure arrangement; in which the identification band is configured to evidence tampering when removed.

Some embodiments provide an apparatus that includes a first identification band that includes a first unique serial number or other identifier, a second identification band that includes a second unique serial number or other identifier, and a third bridging identification band that connects the first and second identification bands, in which the first and second identification bands show evidence of tampering upon removal.

In some embodiments, a system is provided that includes a first identification band, a second identification band; a bridging band connecting the first and second identification bands, an oxygen saturation sensor attached to the first identification band, and a sensor signal cable attached to the oxygen saturation sensor, in which the first and second identification bands show evidence of tampering upon removal.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings briefly described below.

DETAILED DESCRIPTION OF THE INVENTION

Figure 1:
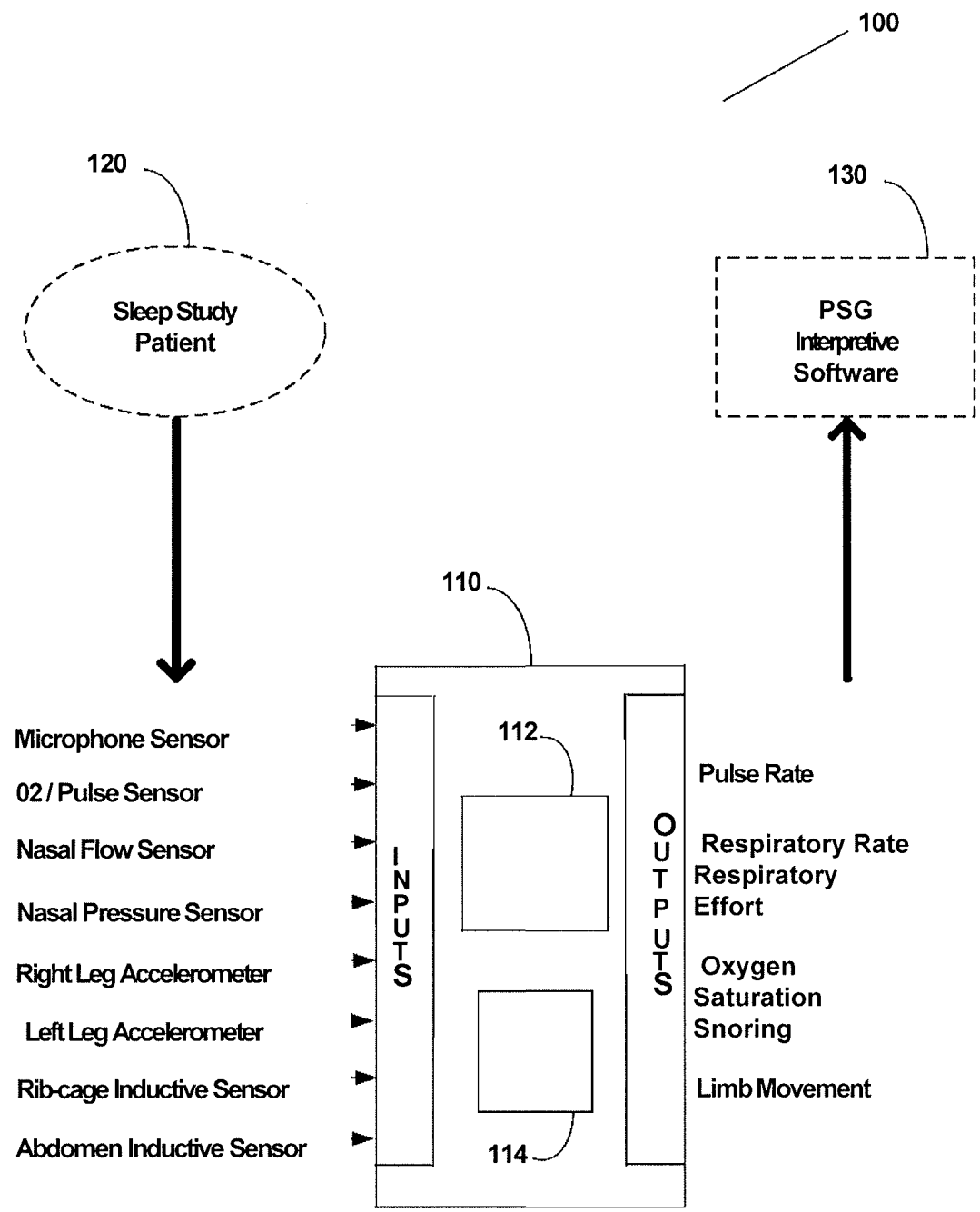
FIG. 1 represents an exemplary portable sleep diagnostic testing and monitoring system in a functional block diagram to show the major components and interfaces for a monitoring and recording instrument that may be employed in accordance with an aspect of the present design.

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to securing a pulse oximetry sensing device (e.g. oxygen saturation sensor), and associated signal cable, using a device such as an identification band, with any of a tearable, shredable and/or one-time securing snap region, for attaching the sensor to the test subject (e.g. patient) during ambulatory sleep monitoring and recording.

The identification band arrangement may fix the sensing device and signal cable to the patient in a manner sufficient to reliably monitor the test subject, by protecting the sensor device from tampering and decreasing the likelihood of potential test fraud during sleep apnea testing. Such operation may occur when a respiratory therapist (e.g. clinician) follows the installation protocol called for herein.

The system disclosed may include, but is not limited to, at least one identification band device that encircles the patient's finger and runs back to the patient's wrist using a secure affixing arrangement with identification numbers in combination with a finger sensor device configured with a signal cable for affixing and positioning the sensor and cable prior to undergoing testing.

The installation protocol further includes providing for accurate test subject identification and education prior to starting the procedure. The present design may involve, but is not limited to, inter looping of two identification bands, requiring a patient to mark his or her identification band, inter looping the signal cable to circle around the identification band, and for applying a shearable tape, such as packing tape, to partially cover the sensor and cable. The methods may include, but are not limited to, securing a cable and/or sensor to the patient using adhesive, plastics, and so forth from one or more identification bands, and recording the identification numbers from the identification bands.

The present design may enable the respiratory therapist to identify evidence, for example a torn identification band or a sheared tape, resulting from an attempt to manipulate the monitored results.

The tamper resistant and secure method for affixing a pulse-oximetry sensor for ambulatory PSG (polysonography) monitoring described herein may be used with other testing devices employing a sensor affixed to the patient. Ambulatory sleep diagnostic testing and monitoring and pulse oximetry may further involve the use of other types of sensors such as accelerometers (measuring limb movement), and inductive bands (monitoring breathing characteristics, such as effort and rate). The methods and protocols disclosed herein may be used for securing these additional sensor types in a generally tamper-proof manner. For example, an accelerometer may be attached to each of the patient's legs, and/or inductive bands may be attached to the patient's chest, secured in accordance with the present design.

The present design may be applied to other forms of ambulatory sensor based monitoring, including for example to document sleep behaviors and patterns, circadian rhythm, respiration measurements, hyper and hypo-activity, and cardiac output that may be associated with study procedures such as found in electrocardiography and electroencephalography.

The present design is not limited to ambulatory testing. For example hospital facilities, in-patient labs, and the military may use the present reliable monitoring system for overnight or "at home" testing. The present design can provide for a safe, comfortable, reliable, and tamper resistant sensor deployment in conjunction with a portable PSG monitoring and recording system.

While the present design may be used in various environments and applications, it will be discussed herein with a particular emphasis on an ambulatory sleep study environment where a respiratory therapist or health care practitioner affixes sensing devices to a patient/test subject prior to conducting a test. For example, one embodiment of the present design is in conjunction with a sleep diagnostic testing, monitoring and recording medical system that comprises an independent recorder module and pulse-oximetry sensor device connected by a signal cable.

FIG. 1 illustrates a functional block diagram of a portable sleep diagnostic test medical system 100 including the major components and interfaces for a monitoring and recording instrument that may be employed in accordance with the present design. Portable sleep diagnostic test recorder 110 may receive multiple communication signals delivered from individual cables attached to sensors positioned on sleep study patient 120. The signals may be received from a microphone sensor, an oxygen saturation/pulse sensor, nasal flow and pressure sensors, right and left leg accelerometers, and/or inductive sensors placed at the abdomen and at the rib cage.

Portable sleep diagnostic test recorder 110 may include processor 112 and memory 114 to monitor and record the received input sensor signals. Sleep diagnostic test recorder 110 may process the received communication signals and convert the signals into data and information readable by interpretive software 130.

Interpretive software 130 may receive the communication signals from the sleep diagnostic test recorder and present the information on a display monitor device for review by the respiratory therapist, doctor, or other appropriate individual. The interpretive software may receive information from sleep diagnostic test recorder 110 and present graphical representations and/or cumulative results for monitored patient's pulse rate, respiratory rate and effort, oxygen saturation, snoring, and limb, (e.g., leg, movement, and so forth).

Figure 2:
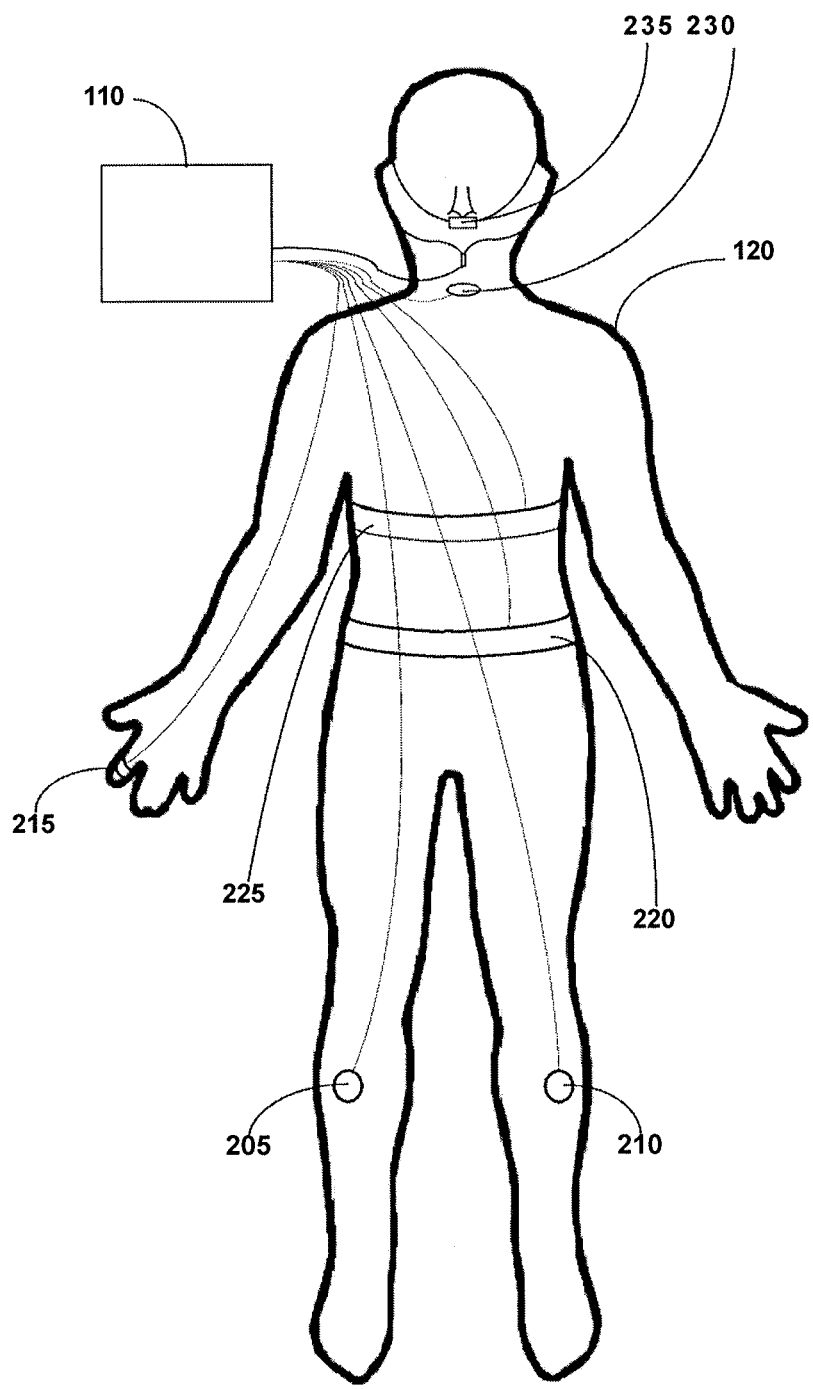
FIG. 2 shows a portable sleep diagnostic testing and monitoring system configured to receive signals from an array of sensors affixed to a patient for sleep apnea monitoring.

FIG. 2 illustrates a portable sleep diagnostic test polysomnography medical system 200 configured to receive signals from an array of sensors affixed to a patient in order to monitor sleep apnea characteristics. This configuration includes right leg accelerometer 205 and left leg accelerometer 210, pulse-oximetry sensor, abdomen inductive sensor 220, rib-cage inductive sensor 225, microphone 230, and nasal flow sensor/pressure sensor 235.

The present design provides a method or protocol for providing reliable oxygen saturation monitoring for ambulatory sleep apnea monitoring. The protocol may provide for relatively secure, tamper evident, uninterrupted measuring, and an efficient and effective means for managing ambulatory testing. The protocol may provide education and specific instructions to the patient prior to test conduct.

The present design may involve a Type 1 Monitoring device configured for use during in-lab polysomnography monitoring, or may involve a Type 2, 3, or 4 Monitoring device configured for use during ambulatory polysomnography monitoring.

Before commencing with testing, the present design may involve educating the patient by explaining the reasons behind the protocol and procedures about to be used. Education may include, but is not limited to, discussing the need for reliable results, addressing situations where previous patients have invalidated their results, such as switching the sensor device with another individual, obtaining a baseline measurement for comparison and validation of test outcome, in the context of preventive measures that ensure the accuracy of the test results.

Figure 3A:
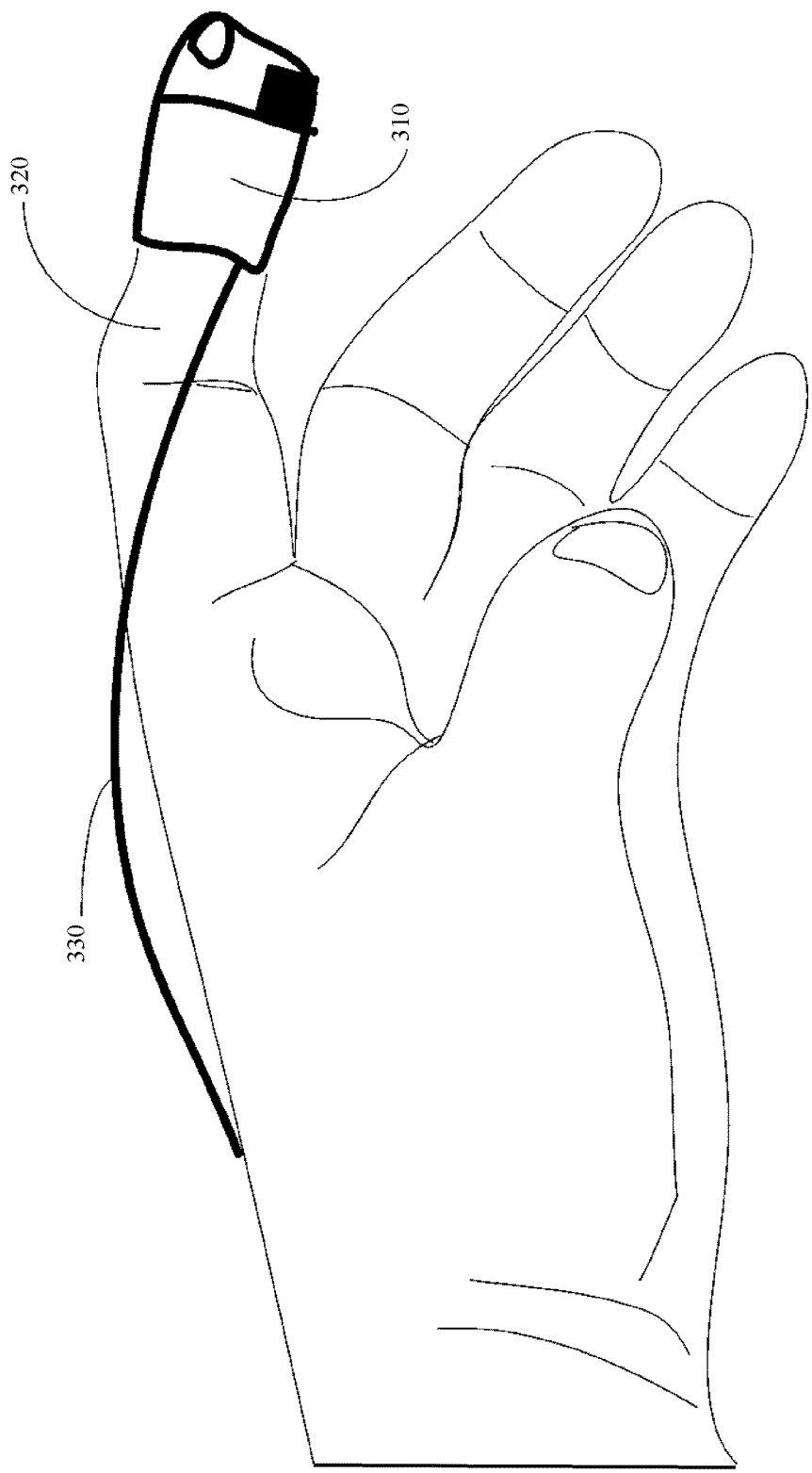
FIG. 3A illustrates a generalized view of an exemplary oxygen saturation sensing device design for use in sleep study monitoring.

FIG. 3A illustrates a generalized view of an exemplary oxygen saturation sensing device design for use in sleep study monitoring. The present design may be configured to work with currently approved Type II, Type III, and Type IV pulse-oximetry oxygen sensing devices.

A respiratory therapist, doctor, registered polysomnographic technologist, clinician, or other operator may position oxygen sensor 310 over patient's finger 320 and attach the sensor, which may be employing an adhesive backing mechanism, in accordance with directions for employing the sensor. Oxygen sensor 310, such as a pulse-oximetry sensor, may communicate signals to a PSG recorder over signal cable 330. Signal cable 330 may be routed along the hand, backside of wrist, and along the arm of the patient in a comfortable manner, such as using the patient's non-dominant arm. The respiratory therapist may check the patient's commercial or regular driver's license, passport, and like documentation to positively confirm patient's identity, and record the identifying information on a test form. In addition, the therapist may record serial numbers from one or more identification bands and the date and time of study. The therapist may ask the patient to review the test form for accuracy and then sign the form.

Figure 3B:
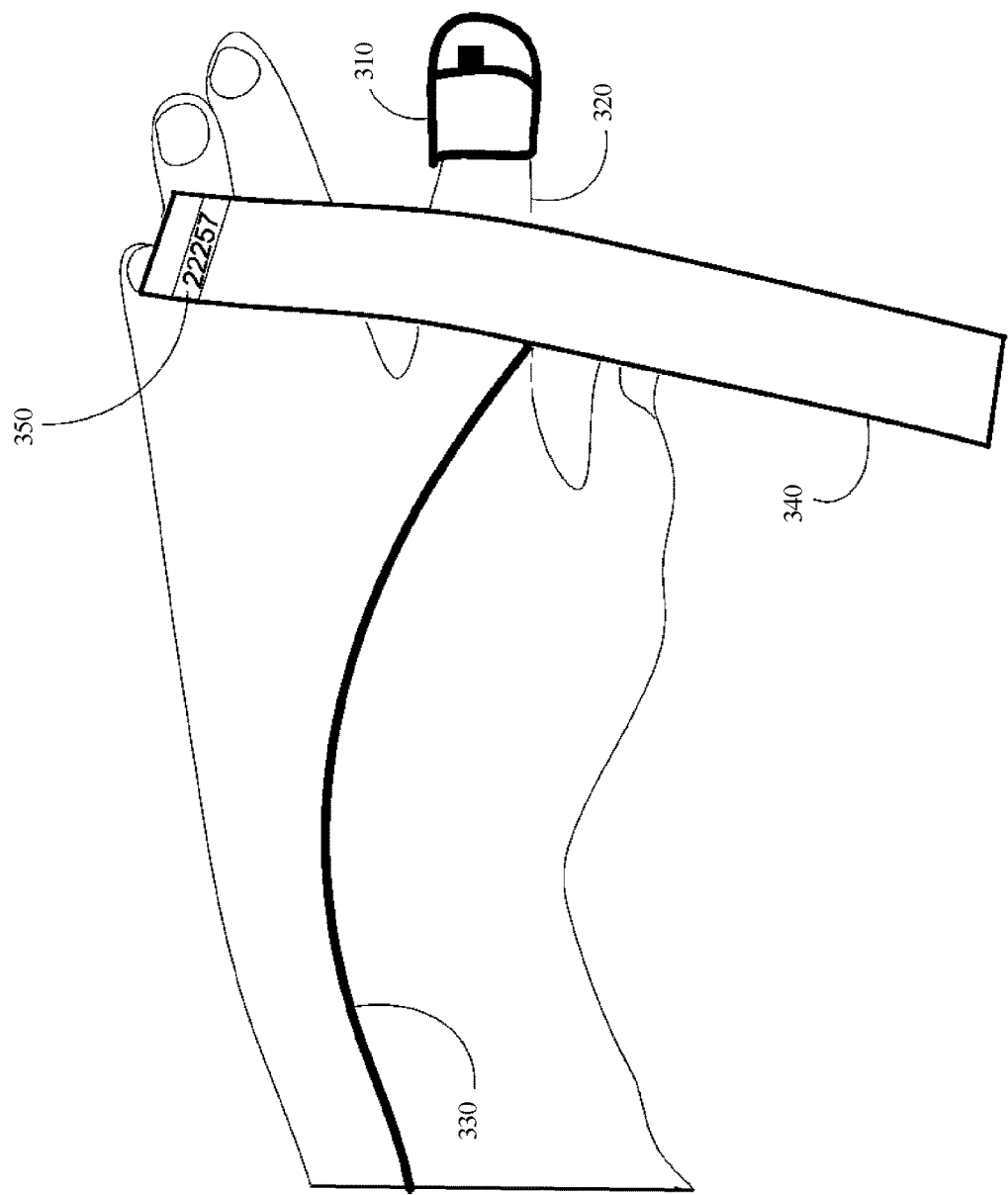
FIG. 3B is an exemplary identification band positioned to cover a oxygen saturation sensing device signal cable and lay across a patient's finger.

FIG. 3B illustrates an exemplary identification band positioned to cover an oxygen saturation monitoring device signal cable and lay across a patient's finger. The identification bands used may include tamper-proof bands. The identification bands may be any suitable identification band including those that are non-abrasive, malleable, tamper resistant or tamper evident. In one embodiment, the present design may involve identification bands exhibiting unique serial numbers, markable such as by using a pen, and the band's material shreds and/or tears when removed. With respect to the serial numbers and markings used to distinguish the identification bands, unique is meant to indicate that the serial number or markings are unusual, not common, or not easily reproduced. That is to say that a patient would not be able to easily remove an identification band and replace it with another with the exact same serial number or markings, and thus defeat the fraud mitigation system. Suitable materials for constructing the disclosed identification bands may include, but is not limited to, Tyvek® (flashspun high-density polyethylene fiber material), plastic, vinyl, polyvinyl chloride (PVC), and various metals and fabrics. The present design may configure one of these materials, or a combination of these materials, for exhibiting tampering evidence when removed, such as tear marks resulting from being torn and shredded during removal.

Identification band 340 is positioned over the patient's finger 320 where oxygen sensor 310 is attached. The respiratory therapist may lay identification band 340 in a near perpendicular relationship to the patient's finger and arranged to cover signal cable 330. FIG. 3B illustrates the identification bands integral serial number 350 facing outward in a manner for easy viewing.

Figure 3C:
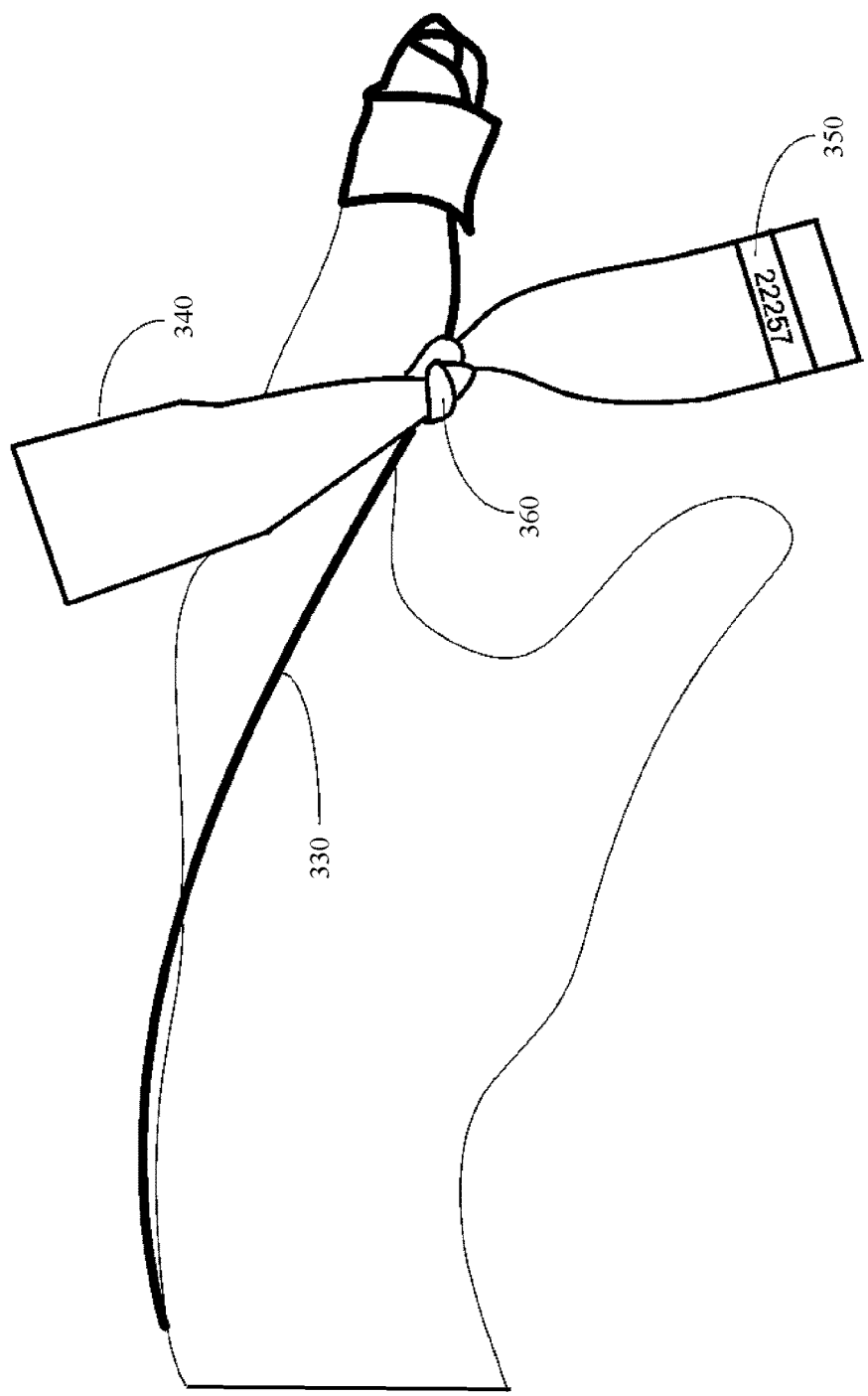
FIG. 3C represents an identification band tied in a knot around the oxygen saturation sensing device signal cable positioned at a patient's finger.

FIG. 3C illustrates an identification band tied in a knot around the oxygen saturation sensing device signal cable positioned at the patient's finger. The respiratory therapist may configure identification band 340 by forming a loop arrangement available for routing signal cable 330 through the loop and then tighten the loop creating knot 360 in the identification band encircling around the signal cable. Knot 360 may include, but is not limited to, types such as overhand, clove hitch, sheet, bowline, and figure eight. Independent of the knot type employed, proper tying and securing are paramount to successful deployment. As an alternative to the knot, the signal cable can be secured to the band with the adhesive section of the band, or snaps, loops, or the like.

Figure 3D:
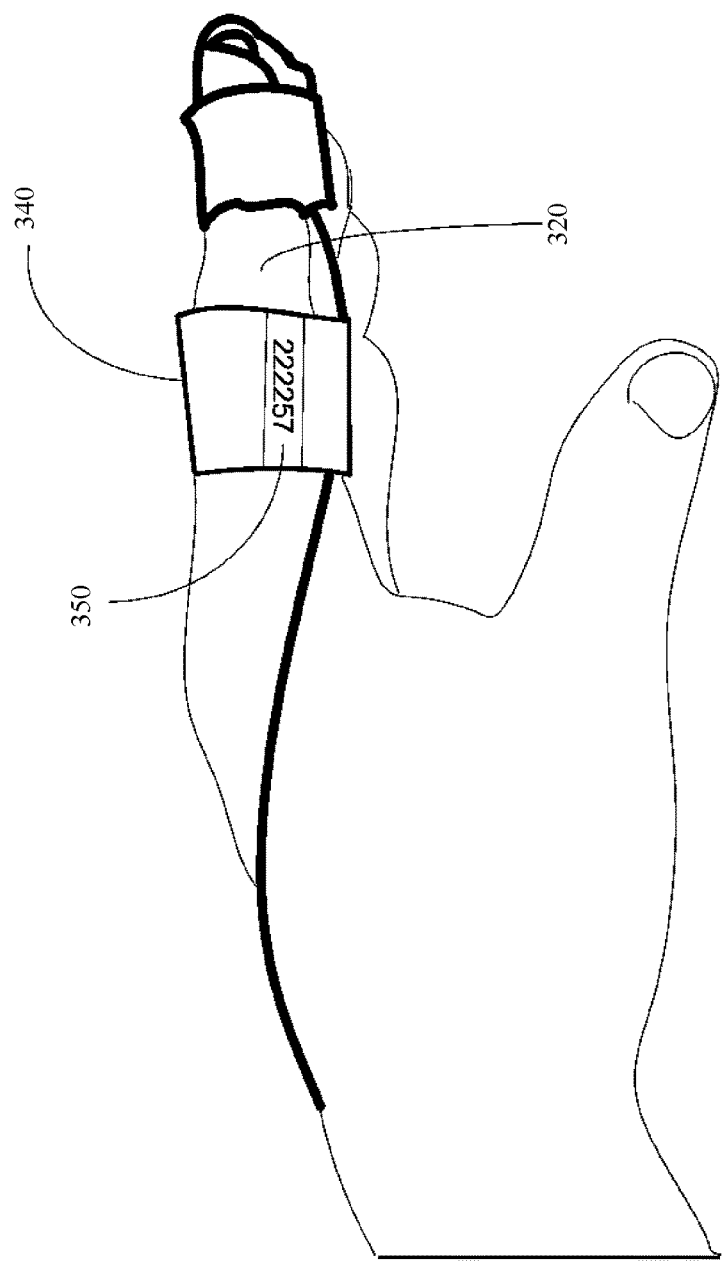
FIG. 3D is an identification band affixed to itself and in an arrangement to position the identification number for viewing by a register therapist.

FIG. 3D illustrates identification band 340 affixed to itself and in an arrangement to position serial number 350 for viewing by appropriate personnel, such as a respiratory therapist. After the knot is tightened around the signal cable, sufficient for securing the band to the cable, the respiratory therapist may wrap each end of identification band 340, in opposite directions, to encircle patient's finger 320. In the case of an adhesive based band, the therapist may remove the protective backing and affix the band ends together. Other band types may be affixed to the patient according to the band manufacturer instructions. For example a band that employs a single snap on one end of the band, and provides a mate to the snap at the opposite end of the band, may entail the therapist aligning the snap with the mate to affix the band.

The present design may provide a secure, proof-positive, and uninterruptable sensor device-to-patient arrangement, sufficient for realizing reliable oxygen saturation measurements.

Figure 3E:
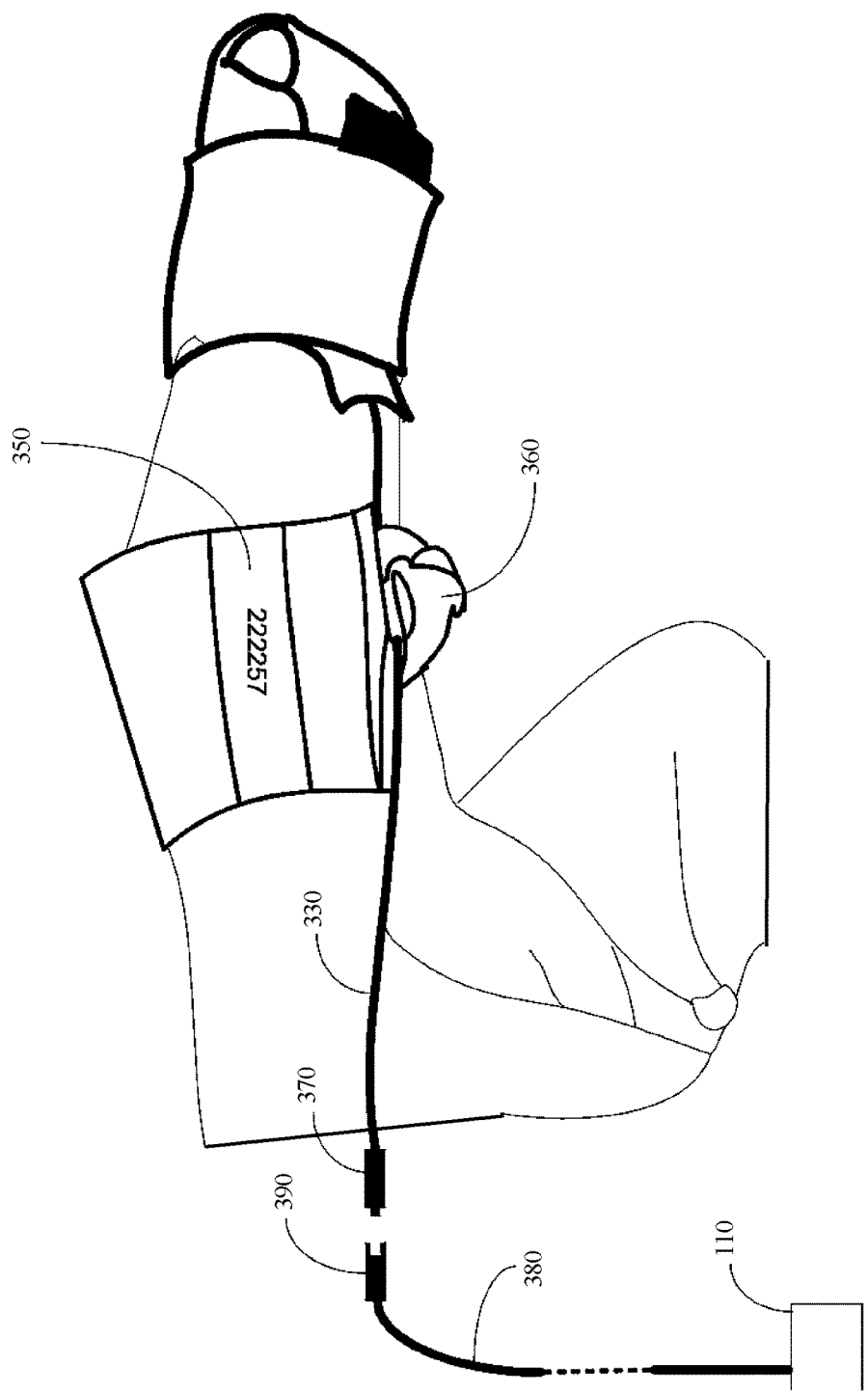
FIG. 3E shows a close up perspective view of the signal cable passing through a knot formed by the identification band.

FIG. 3E is a close up perspective view of signal cable 330 passing through knot 360 formed by affixing the band ends together in accordance with the method disclosed herein. Signal cable 330 may provide connector 370 for attaching signal cable 380 at connector 390 to communicate sensor signals for monitoring and recording by portable PSG recorder 110. Prior to test conduct, connector 370 is joined with connector 380 to complete the signal path. Serial number 350 is shown positioned for easy viewing by a register therapist. In another embodiment, the therapist may add a separate identification band by where the band is looped around the connection of signal cable 330 and the PSG recorder signal cable 380 where the cables meet and connect via connector 370 being plugged into connector 390. As an alternative to the knot, the signal cable 330 can be secured to the band placing it directly under the adhesive section of the band, which may be under the serial number 350, or with other securing methods such as snaps, loops, or the like.

The present design may involve the therapist recording a baseline pulse measurement as a further identity check prior to ambulatory test conduct. The baseline pulse measurement may be use as a profile for checking the test results. The check may include matching the patient's test results with the previously recorded baseline measurement. In the situation where the profile does not match the test results, the test outcome is deemed unreliable.

Figure 4A:
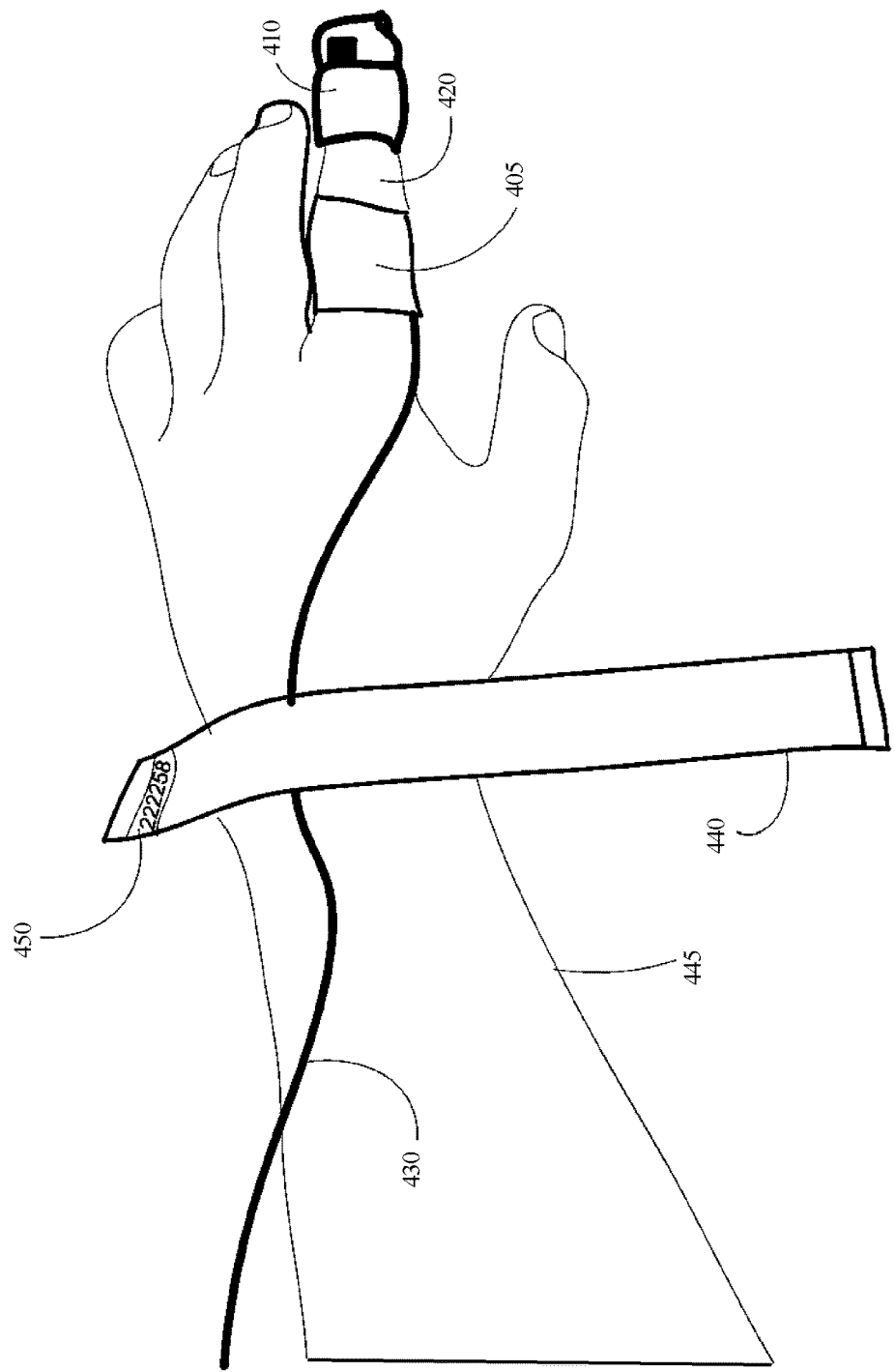
FIG. 4A illustrates an exemplary identification band positioned to cover the oxygen saturation sensing device signal cable and lay across a patient's wrist.

FIG. 4A illustrates an exemplary identification band positioned to cover the oxygen saturation sensing device signal cable and lay across a patient's wrist. The identification bands may be tamper-proof, numbered using a unique serial number, and/or designed to shred and/or tear when removed, such as the band types previously described and shown in FIGS. 3B-3E. Identification band 405 and pulse-oximetry sensor device 410 are shown attached to finger 420.

Identification band 440 is positioned over the patient's wrist 445 and signal cable 430 originating from sensor device 410. The respiratory therapist may lay identification band 440 in a near perpendicular relationship to the patient's wrist and arranged to simultaneously cover signal cable 430. FIG. 4A illustrates the identification band's integral serial number 450 facing outwards in a manner for easy viewing.

Figure 4B:
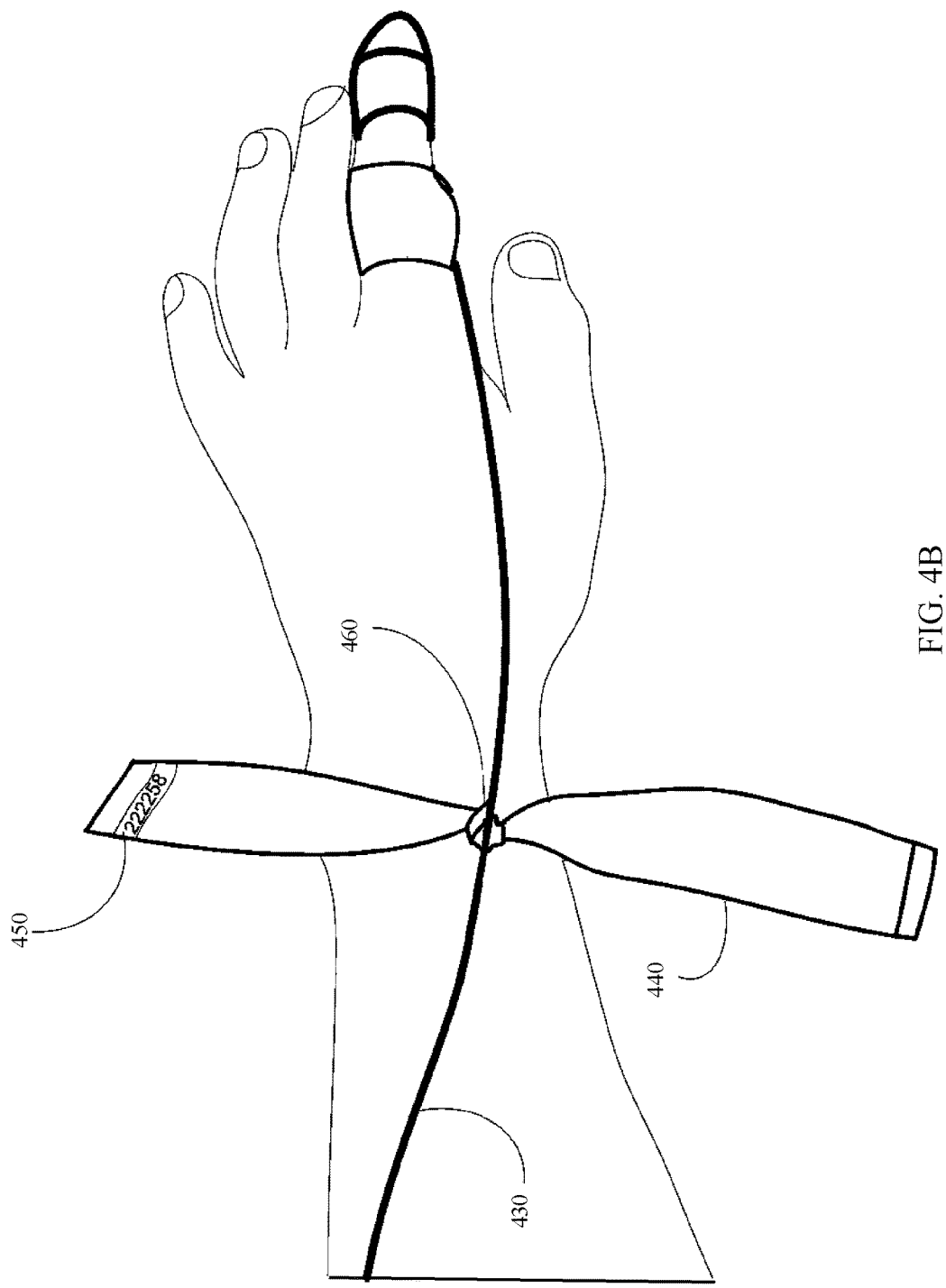
FIG. 4B represents an identification band tied in a knot around the oxygen saturation sensing device signal cable positioned at the patient's wrist.

FIG. 4B illustrates an identification band tied in a knot around the oxygen saturation sensing device signal cable positioned at the patient's wrist. The respiratory therapist may configure identification band 440 by forming a loop arrangement available for routing signal cable 430 through the loop and then tighten the loop creating knot 460 in the identification band encircling around the signal cable. The therapist may ensure knot 460 is properly tied and secured prior to placing in-use.

Figure 4C:
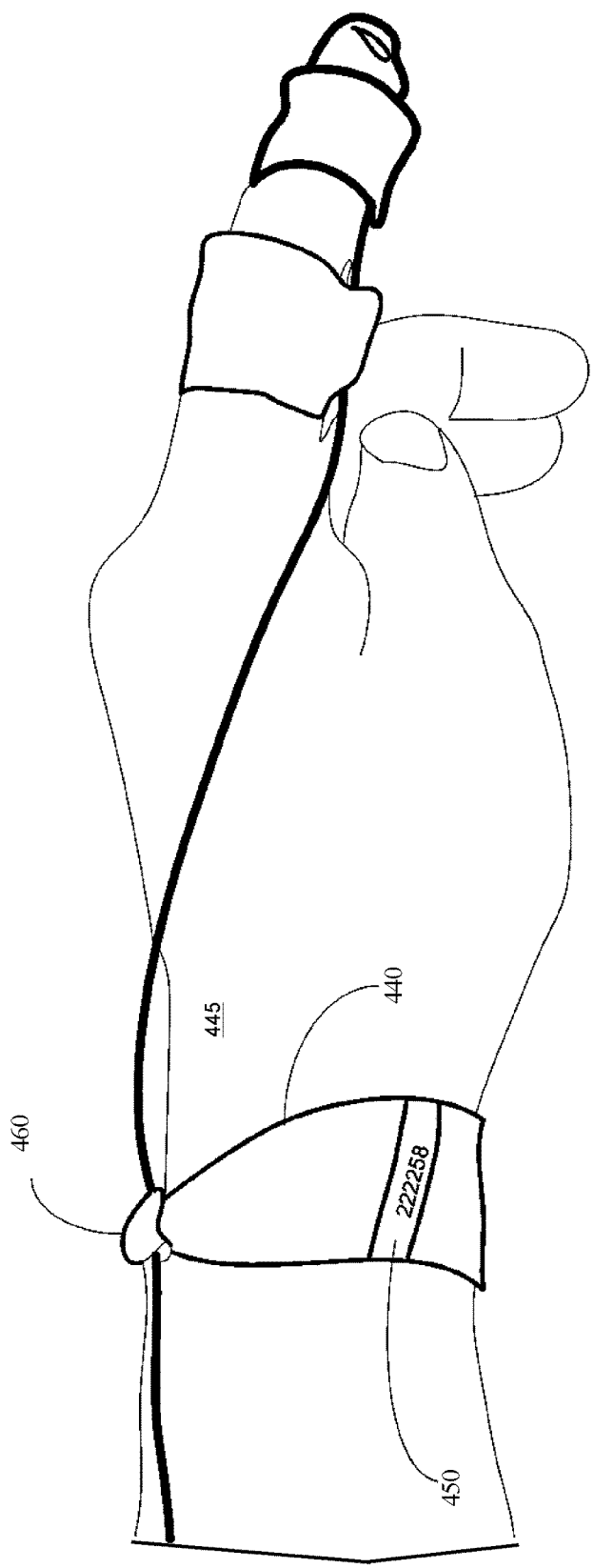
FIG. 4C shows an identification band affixed to itself and arranged to position the serial number for viewing by a respiratory therapist.

FIG. 4C illustrates identification band 440 affixed to itself and arranged to position serial number 450 for viewing by a respiratory therapist. After the knot is tightened around the signal cable, sufficient for securing the band to the cable, the respiratory therapist may wrap each end of identification band 440, in opposite directions, to encircle patient's wrist 445. As an alternative to the knot, the cable can be secured to the band with the adhesive section of the band, or snaps, loops, or the like. Band types may be affixed to the patient's wrist in according to manufacturer instructions.

Figure 4D:
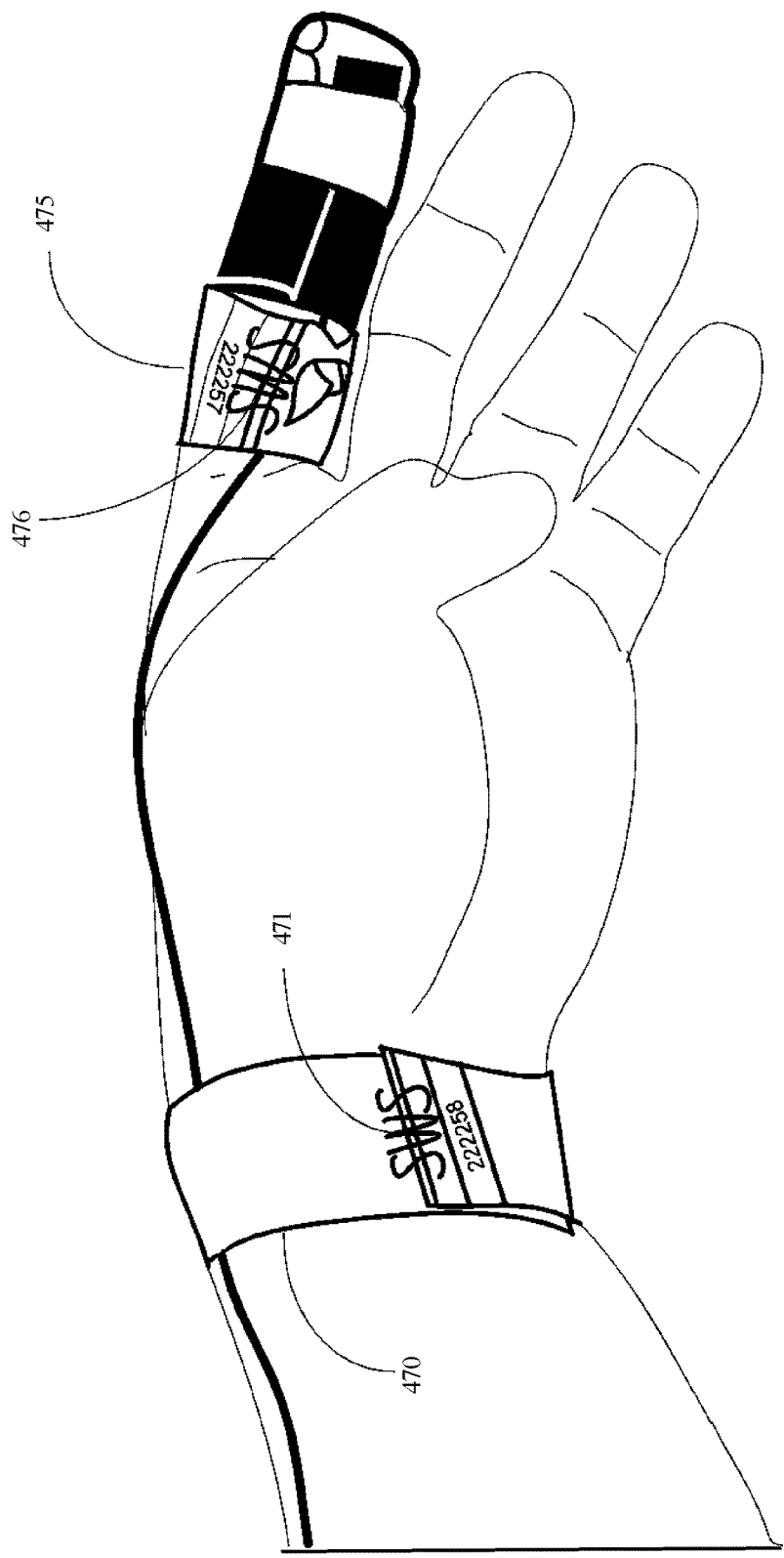
FIG. 4D illustrates a first and second identification band, each marked by the patient, in an arrangement to position a first and second serial numbers for viewing by a respiratory therapist.

FIG. 4D illustrates a first and second identification band, each marked by the patient, in an arrangement to position a first and second serial number for viewing by a respiratory therapist. In this embodiment, identification band 470 is marked at point 471 and identification band 475 is marked at point 476. For example the patient under test, such as a commercial truck driver, may mark each identification band with their signature or other mark for ensuring a "chain of custody" is established. The individual overseeing the test may mark the identification bands, either separate from or in combination with the patient's mark for improving test reliability.

Figure 4E:
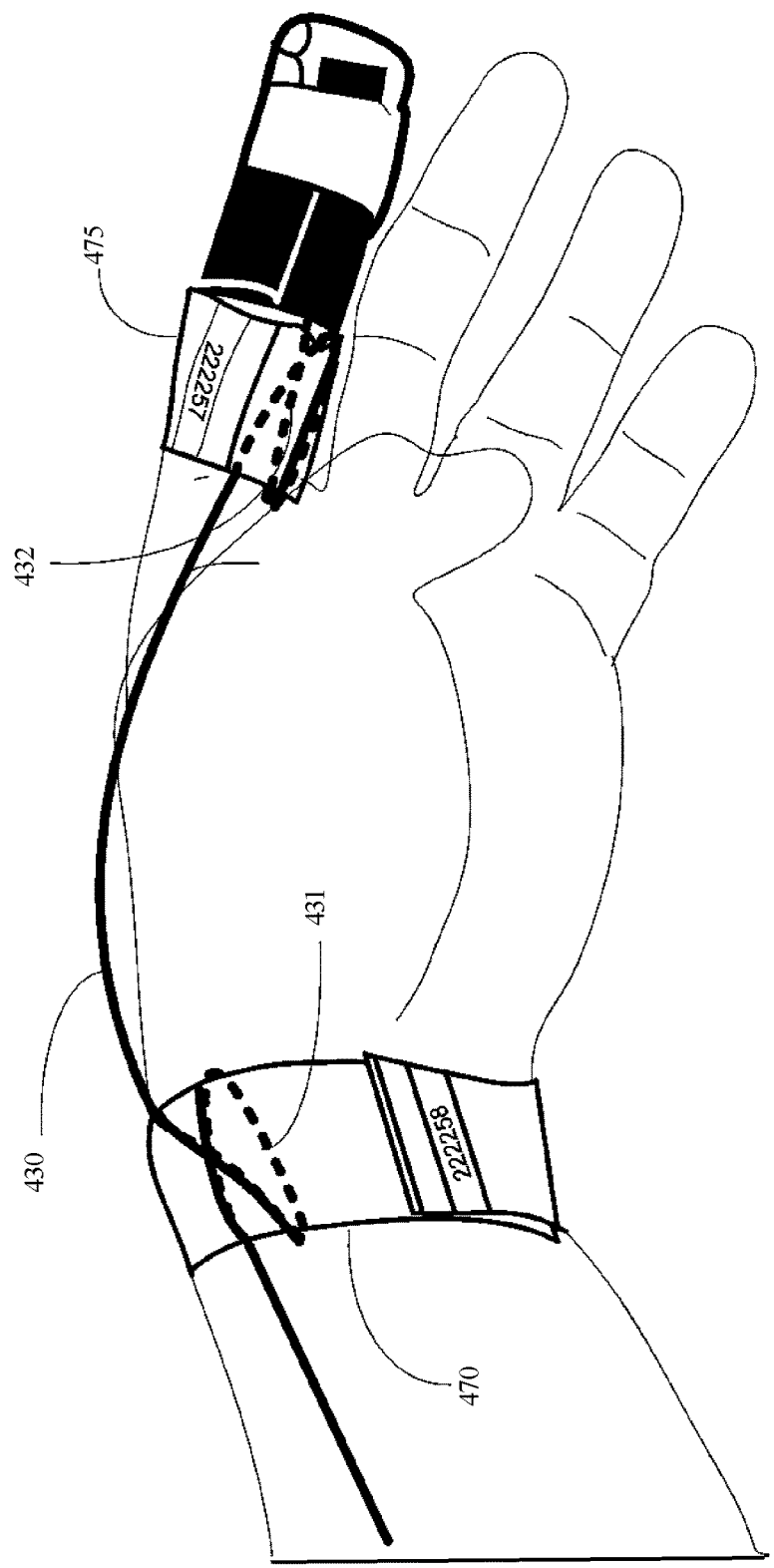
FIG. 4E is a perspective view illustrating a loop formed by a signal cable circling around a first identification band affixed at the finger, and a loop formed by the signal cable circling around a second identification band affixed at the wrist.

FIG. 4E is a perspective view illustrating a loop formed by a signal cable circling around a first identification band affixed at the finger, and a loop formed by the signal cable circling around a second identification band affixed at the wrist. FIG. 4E illustrates a further embodiment of the present design where the therapist may loop signal cable 430 around identification band 470 at point 431. In combination with or separately the therapist may loop signal cable 430 around identification band 475 at point 432, again for improving test reliability.

Figure 4F:
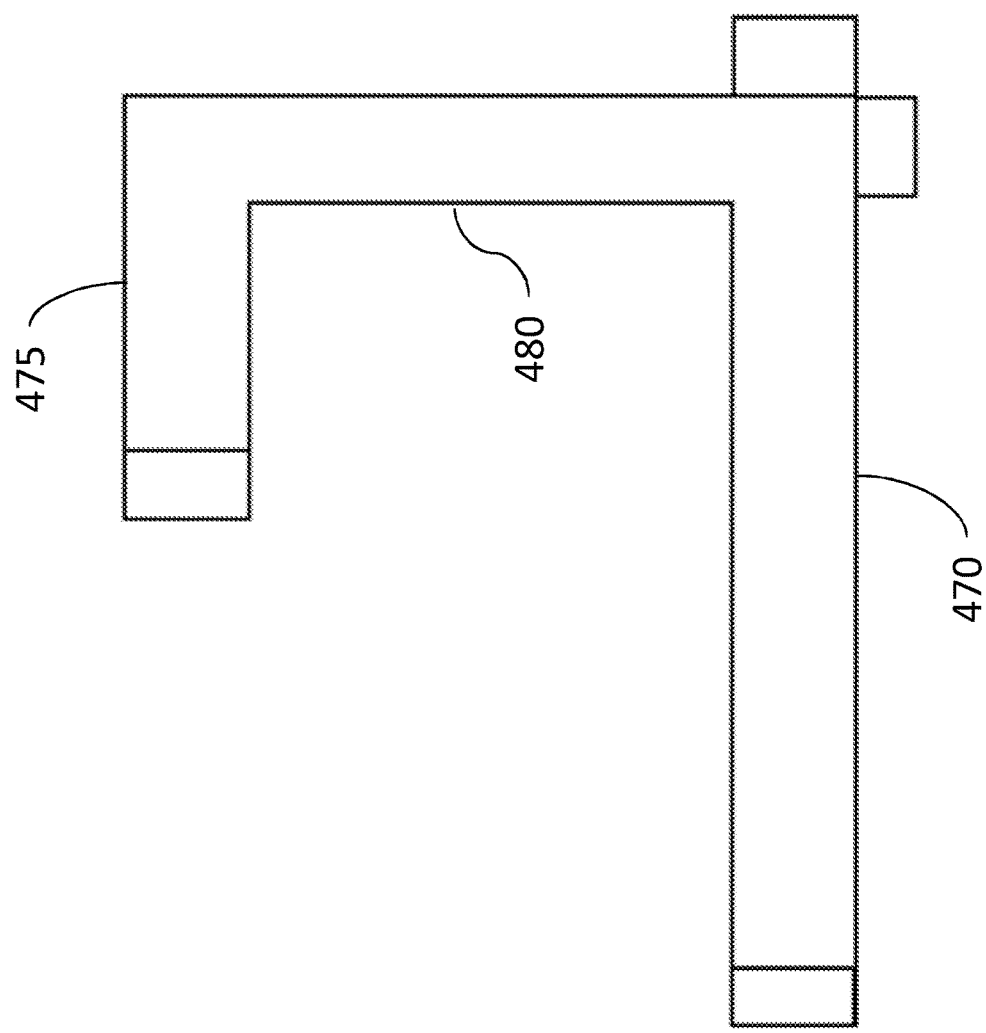
FIG. 4F is a view of an exemplary configuration of identification bands in which there is a smaller identification band to fit around a patient's finger, a larger one to fit around a patient's wrist and a third bridging identification band connecting the other two bands, in which the bridging band may ensure that the finger band cannot be removed or slipped off over a patient's knuckle.

FIG. 4F shows an exemplary configuration of two identification bands joined together by a bridging identification band 480. The bands are shown before affixing to the patient. The smaller identification band 475 may be a pediatric identification band or a standard identification band cut to size. The larger identification bands, the ones used to encircle a patient's wrist 470 and to bridge 480 the wrist and finger identification bands, may be of the same material or different material. The connection between the three bands may be made through the adhesive manufactured on the bands or additional adhesives or attachment devices, such as staples, may be used.

The bridging identification band 480 may be replaced by another type of material that will be resistant to tearing but show evidence of tampering, such as bands that irreversibly snap together, tape or material treated with pressure sensitive ink, plastic that irreversibly deforms when strained, or a combination of such materials. Serial numbers, which are used as distinguishing marks and are described above, may be present on the identification bands which help to verify that the same identification bands are present at the conclusion of a test as at the beginning of the test. The serial numbers may be placed to show tampering with the connection between the three identification bands. In other words, if the serial numbers are misaligned, do not match, or otherwise do not appear as they did prior to the start of the test, this shows evidence of tampering.

Figure 4G:
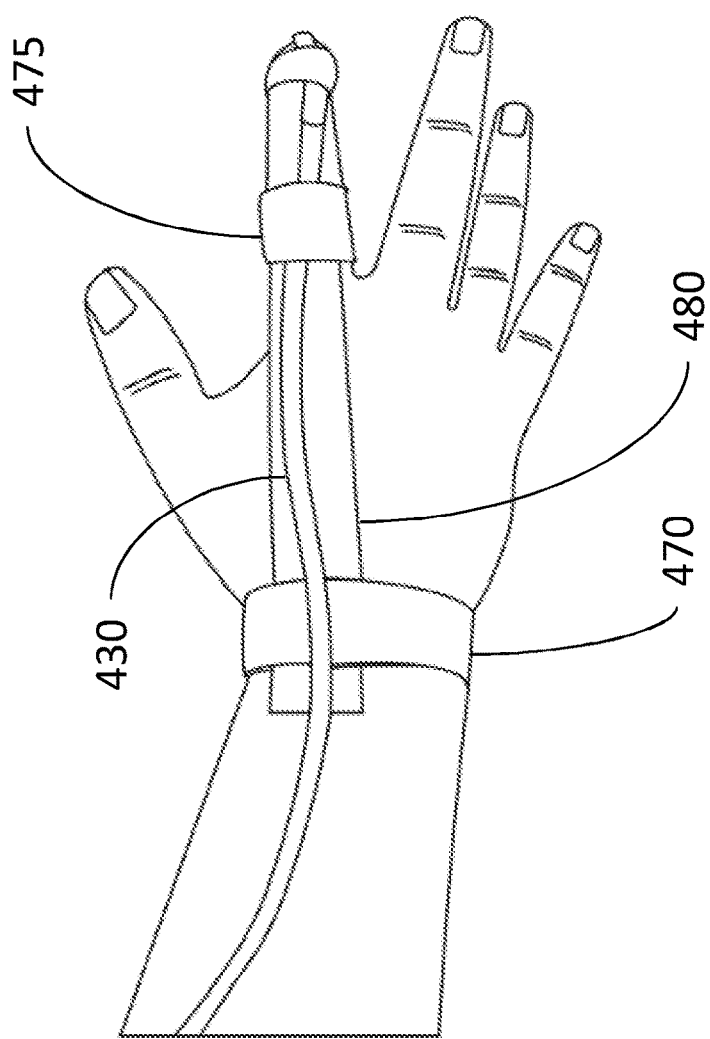
FIG. 4G illustrates an identification band fitted around a patient's finger and an identification band fitted around a patient's wrist joined by an identification band used as a bridging element with the signal cable secured under the bands around the patient's wrist and finger.

FIG. 4G is a representative depiction of a first identification band secured at the finger 475 of a patient and a second identification band secured at the wrist 470 of a patient with a third bridging identification band 480 used to join the first and second bands. The third bridging band 480 may be placed under the signal cable 430, as shown, or over the signal cable.

The adhesive of the third bridging band 480 may be used to secure the signal cable 430 in place with respect to the first and second identification bands, 470 and 475. When the adhesive of the third bridging band 480 is used to secure the signal cable 430, a knot or loop securing any of the identification bands to the signal cable 430 may not be necessary.

The third bridging band 480 may serve to maintain the relative position of the first 475 and second 475 bands, as shown in FIG. 4G. For example, maintaining the relative position of the bands about the wrist and finger prevents the band about the finger from being slid off the finger of the patient without evidence of tampering, and in turn may prevent the transferring of the pulse-oximetry sensor device 410 to another person. The third bridging band tears, shreds, necks, delaminates, changes color, or otherwise physically deforms upon tampering. The identification bands and identification band configuration used in this depiction may be used with other systems that utilize a finger-tip pulse-oximetry sensor device.

Figure 5A:
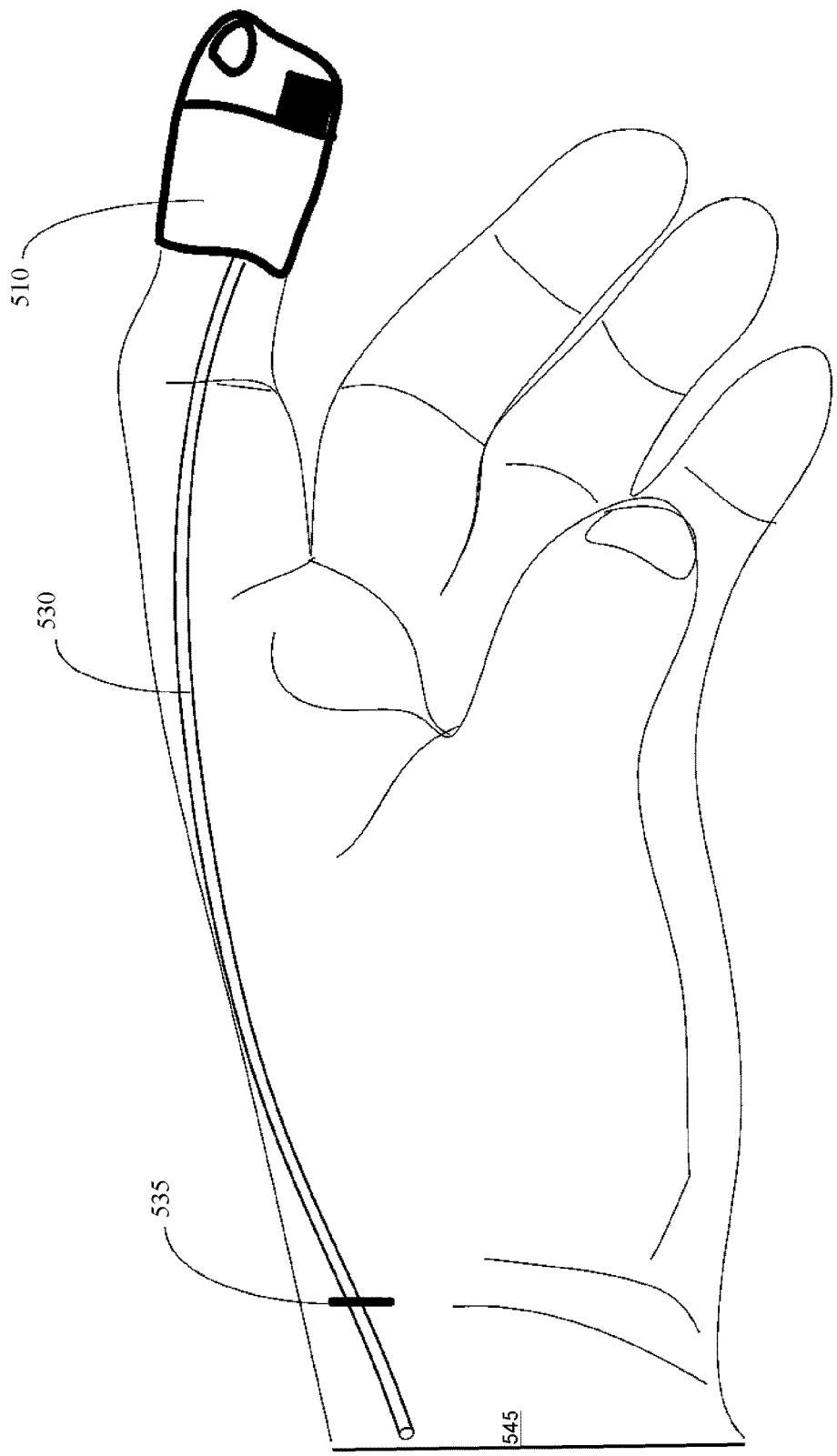
FIG. 5A represents a generalized view of an exemplary oxygen saturation sensing device design indicating where a respiratory therapist marks the signal cable at a crossing point formed when the cable meets a patient's wrist.

FIG. 5A illustrates a generalized view of an exemplary oxygen saturation sensing device design indicating where a respiratory therapist marks the signal cable at a crossing point formed when the cable meets a patient's wrist. In this embodiment the therapist may place mark 535 on cable 530 and patient wrist 545.

Figure 5B:
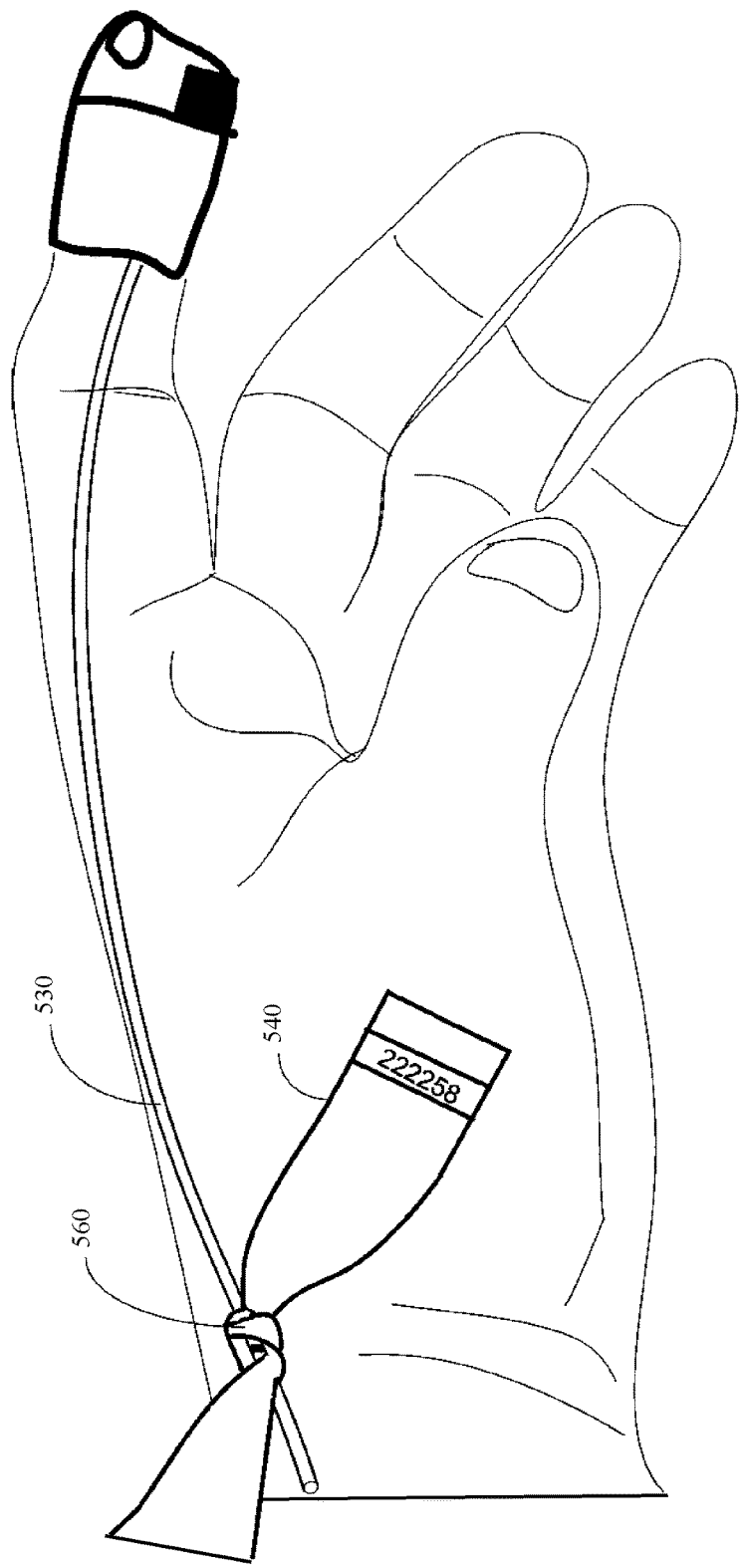
FIG. 5B shows a first identification band tied in a loose knot positioned at the mark on the signal cable.

FIG. 5B illustrates a first identification band tied in a loose knot positioned at the mark on the signal cable.

The respiratory therapist may configure identification band 540 by forming a loop arrangement available for routing signal cable 530 through the loop and then tighten the loop creating loose knot 560 in the identification band encircling around the signal cable.

Figure 5C:
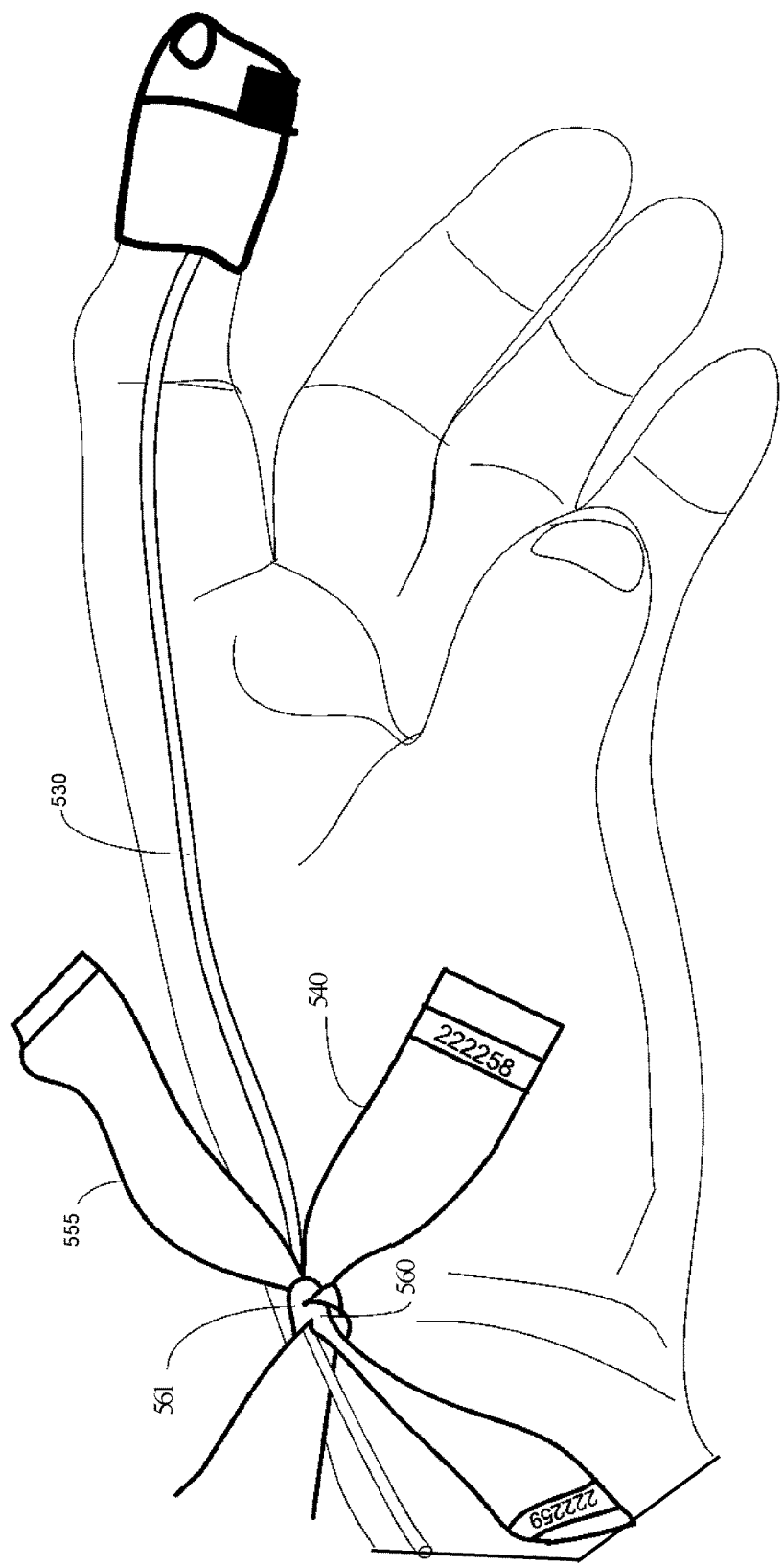
FIG. 5C illustrates a second identification band positioned through the loop formed by the first identification band and tied in a knot positioned at the mark on the signal cable.

FIG. 5C illustrates a second identification band positioned through the loop formed by the first identification band and tied in a knot positioned at the mark on the signal cable. The respiratory therapist may configure second identification band 555 by forming a loop arrangement available for routing signal cable 530 through the loop and then tighten the loop creating knot 561 in identification band 555 encircling around the signal cable. The therapist may ensure identification band 555 is pulled at each end to properly tighten knot 561 and identification band 540 is pulled at each end to properly tighten knot 560 are properly tied, tighten, and secured prior to placing in-use.

Figure 5D:
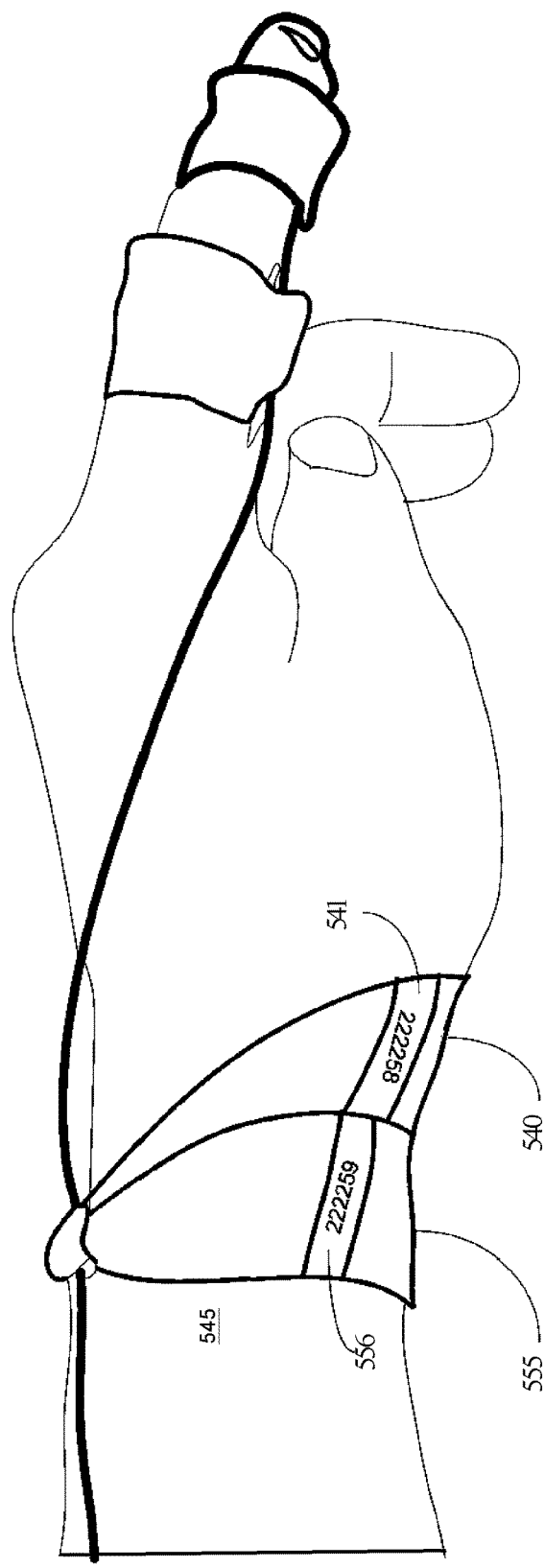
FIG. 5D is a first and a second identification band joined together at the mark on the signal cable and circling a patient's wrist.

FIG. 5D illustrates a first and a second identification band joined together at the mark on the signal cable and circling a patient's wrist. Identification band 540 may be affixed to itself and arranged to position serial number 541 for viewing by a respiratory therapist. After the knot is tightened around the signal cable, sufficient for securing the band to the cable, the respiratory therapist may wrap each end of identification band 540, in opposite directions, to encircle patient's wrist 545. In a similar manner, identification band 555 may be affixed to itself and arranged to position serial number 556 for easy viewing. The respiratory therapist may wrap each end of identification band 555, in opposite directions, to encircle patient's wrist 545. Each band may be affixed to the patient's wrist in according to instructions.

Figure 6A:
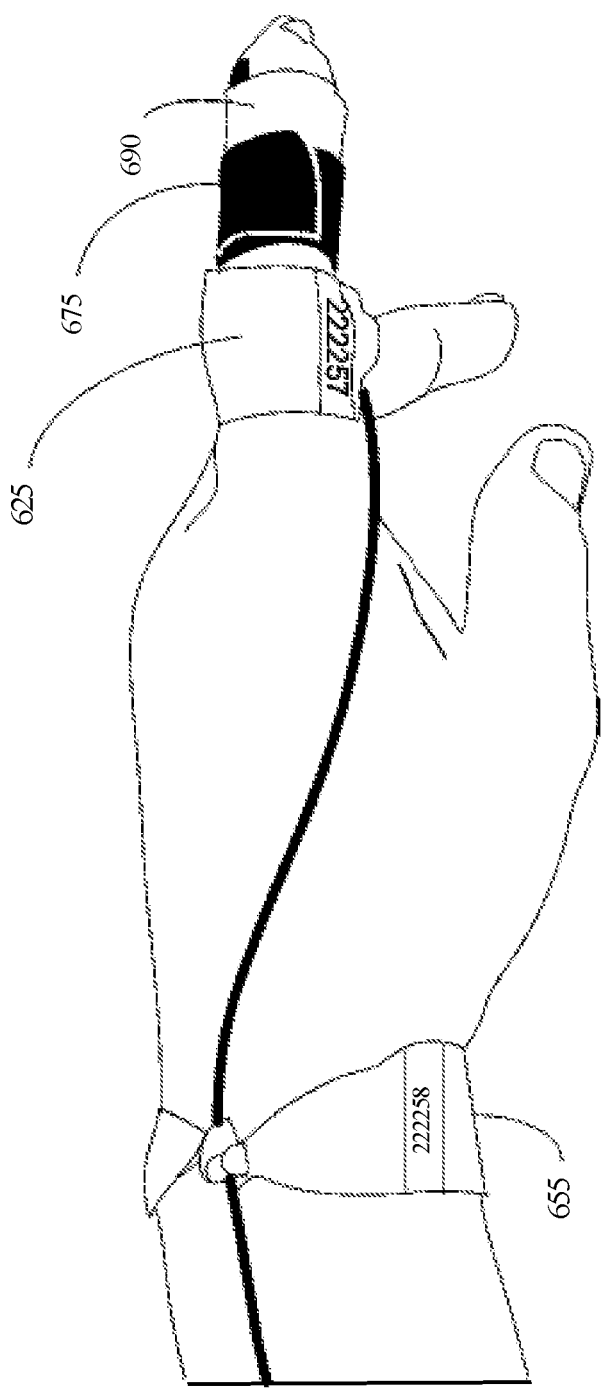
FIG. 6A shows an exemplary design employing two identification bands in combination with a tape, positioned to cover an oxygen saturation sensing device and associated signal cable, wrapped to circle around a patient's finger.

FIG. 6A illustrates a design employing two identification bands in combination with a tape, positioned to cover an oxygen saturation sensing device and associated signal cable, wrapped to circle around a patient's finger. A first identification band 625 may be affixed to the patient's finger and a second identification band 655 may be affixed the patient's wrist as shown.

The identification bands are designed to shred and tear when removed. In this embodiment of the present design, the therapist may wrap tape 675 in a circle around a test individual's finger positioned to cover pulse-oximetry sensor device 690 in combination with simultaneously covering the sensor's signal cable. Tape 675 is constructed from materials used to form the identification bands so that they exhibit shredding and tearing affects on removal.

Although shown using two bands, reliability and security may be realized when using a single band. In general, the present design may realized using at least one band, affixed at either the patient's finger or wrist, and may include any combination and quantity of bands disclosed herein.

Figure 6B:
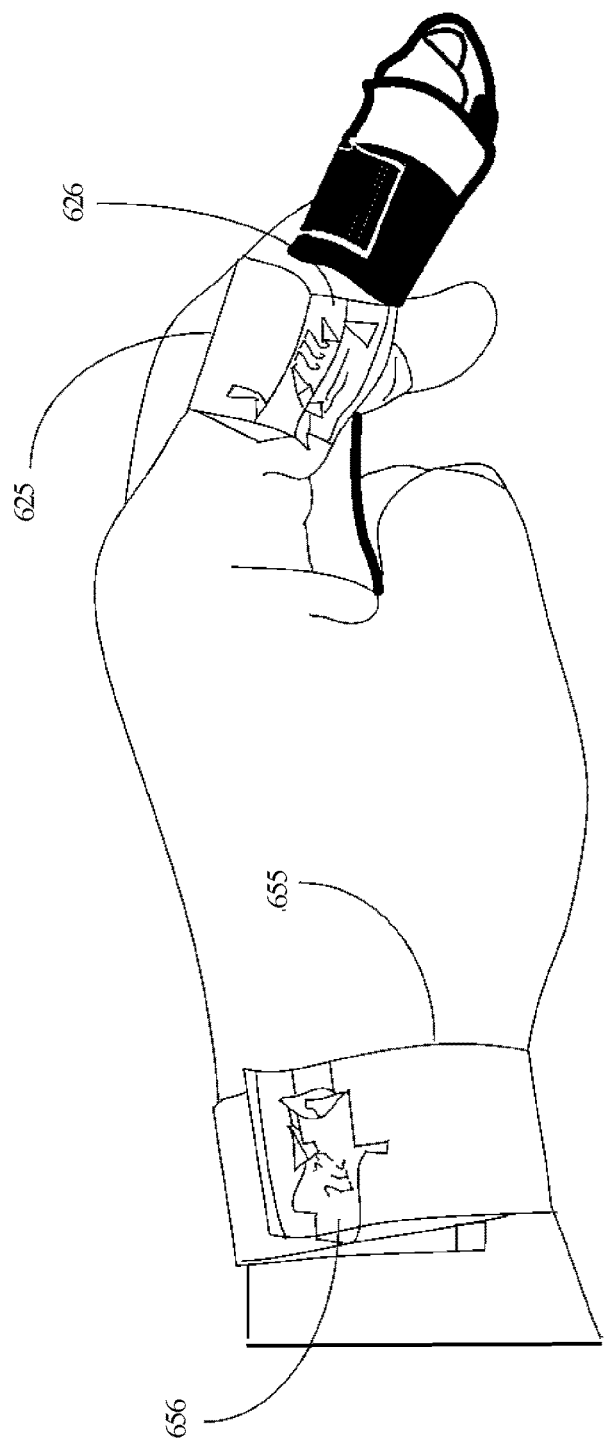
FIG. 6B illustrates a generalized view of two identification bands exhibiting tampering evidence.

FIG. 6B illustrates a generalized view of two identification bands exhibiting tampering evidence. First identification band 625 exhibits evidence 626 of fraud resulting from an attempt to remove the band. In addition, second identification band 655 exhibits evidence 656 resulting from an unauthorized attempt to remove the band.

Figure 6C:
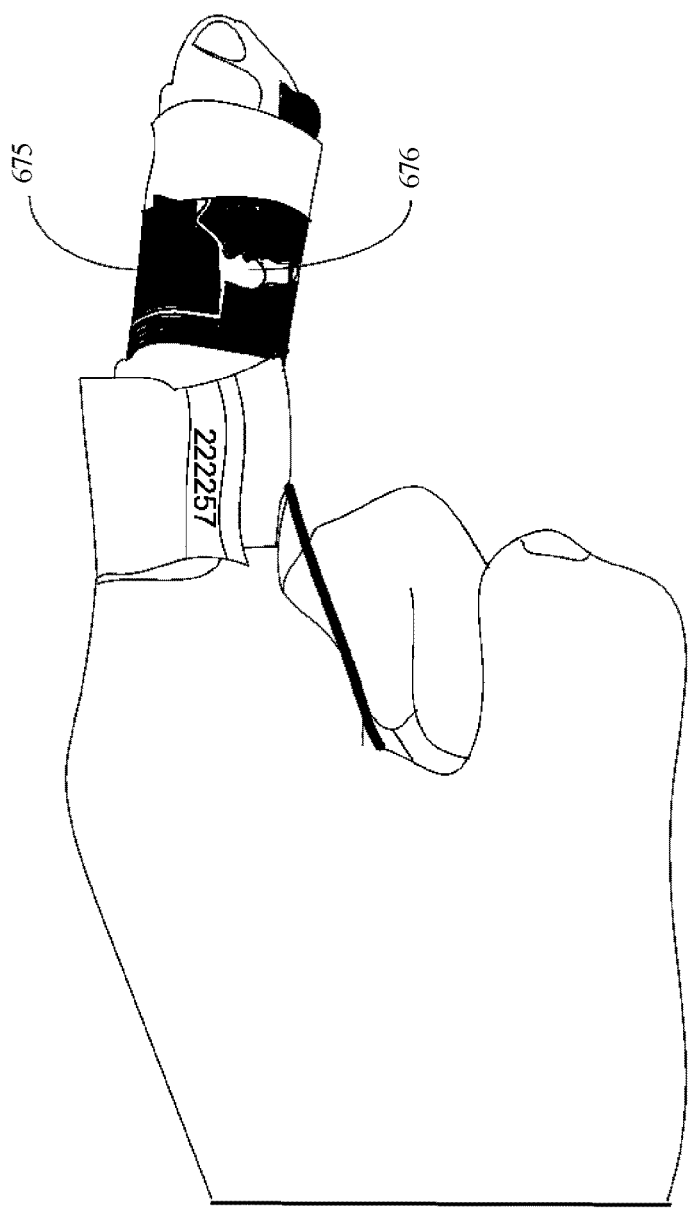
FIG. 6C represents a generalized view of a patient's finger exhibiting a torn tape.

FIG. 6C illustrates a generalized view of a patient's finger exhibiting a torn tape. Tape 675 exhibits evidence 676, in the form of shredding or tearing, resulting from an unauthorized attempt to remove the band.

In this arrangement, the present design may provide for an efficient and financially effective means for providing reliable oxygen saturation monitoring for ambulatory sleep apnea monitoring. The present design's protocol may provide for secure, tamper evident, uninterrupted measuring, for managing ambulatory testing.

Figure 6D:
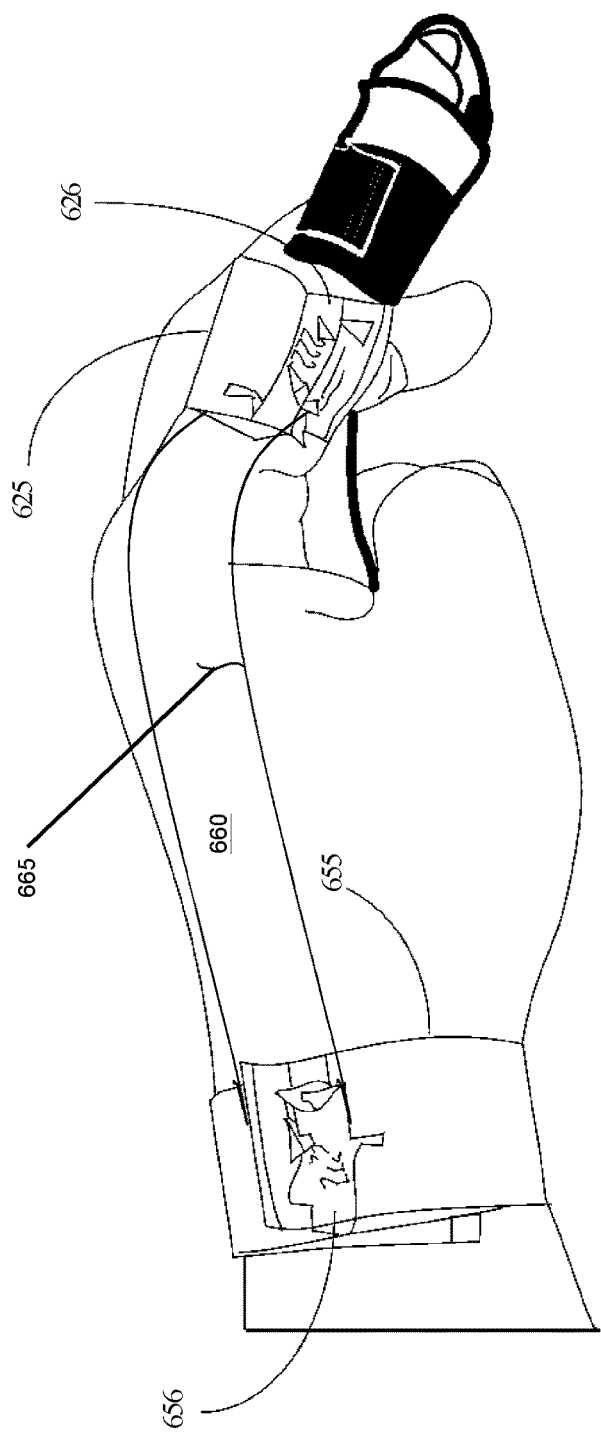
FIG. 6D illustrates a generalized view of two identification bands connected by a third band or other connective element exhibiting evidence of tampering.

FIG. 6D is a generalized view of an identification band at the finger 625 and an identification band at the wrist 655 joined by a bridging band, all showing evidence of tampering. The band at the finger 625 shows tampering evidence from an attempt to remove the band 626. The band at the wrist 655 shows evidence of an attempt to remove the band at the adhesive point 656. The bridging band 660 shows a tear or wrinkle 665 resulting from an attempt to stretch the bridging band.

The bridging band may be comprised of a material different from the other two identification bands. In such cases, signs of tampering may include fraying of the material, stretching or tearing of the material, discoloration, discoloration due to pressure sensitive ink or dye, fraying or detachment of the bridging band at the points where it is joined to the wrist and finger bands, or any combination thereof. The bridging band 660 may also show signs of an attempt to move the oxygen saturation sensor cable when the adhesive of the bridging band is used to hold the sensor cable in place. In such instances, the signs of attempting to move or tampering with the oxygen saturation sensor cable may include the indications listed above for tampering with the bridging band.

Figure 7:
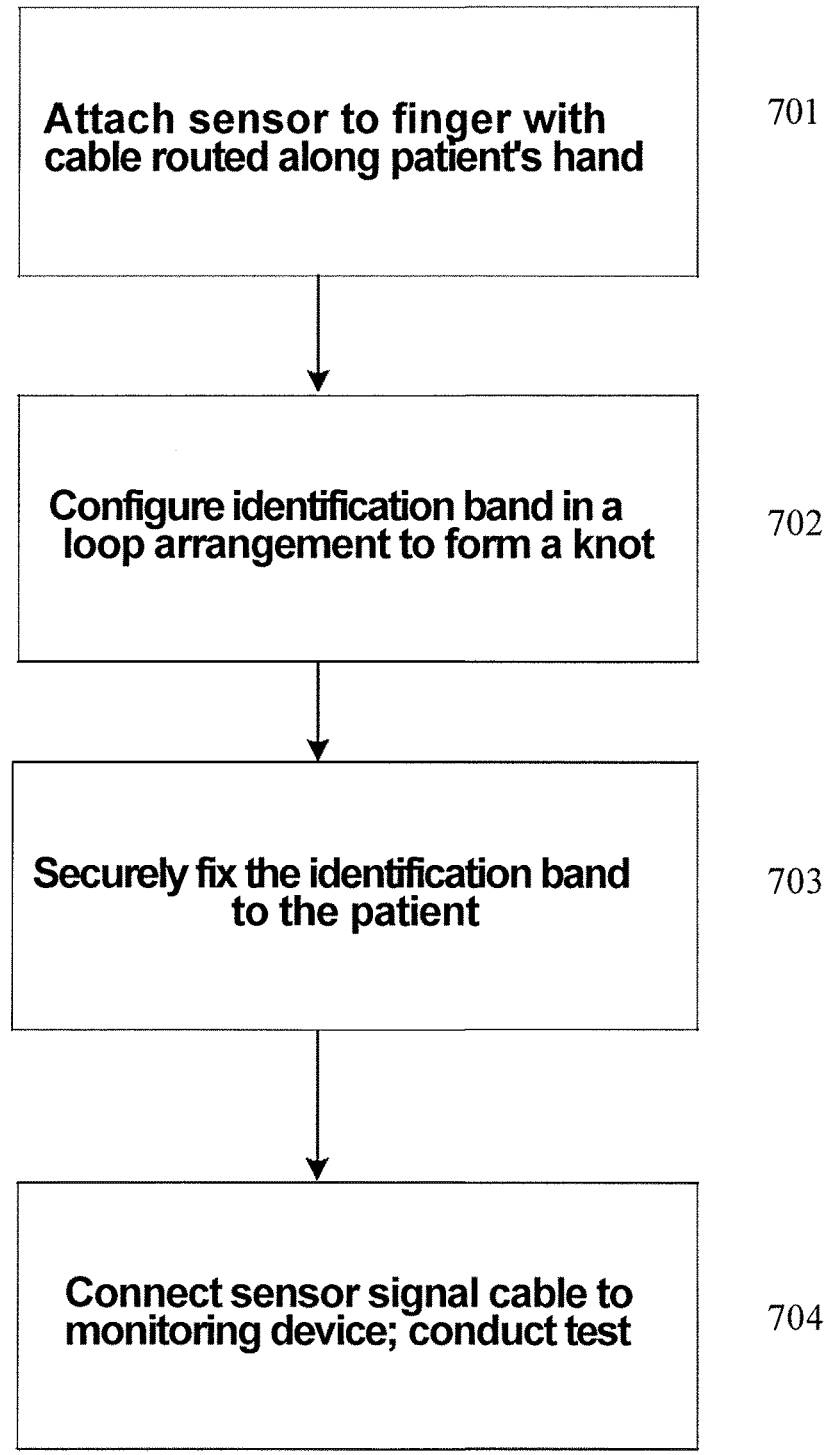
FIG. 7 is a flowchart showing operation according to one embodiment of the current design.

FIG. 7 illustrates the general protocol of the present design. From FIG. 7, box 701 indicates attaching a sensor, such as a pulse-oximetry sensor, to a test subject's finger with a signal cable routed along the patient's hand. Box 702 represents configuring an identification band in a loop arrangement to form a knot where the signal cable is routed through the formed loop. Box 703 indicates securely fixing the identification band to the patient. Box 704 represents connecting a sensor signal cable, such as a pulse-oximetry sensor signal cable, to a monitoring device, such as a portable sleep diagnostic test or polysomnography monitoring system, during test conduct. The identification band is configured to encircle the patient's finger and to shred and/or tear when removed. It should be understood that the cable can be secured to the band with the adhesive section of the band, snaps, loops, or the like, in place of a knot.

Figure 8:
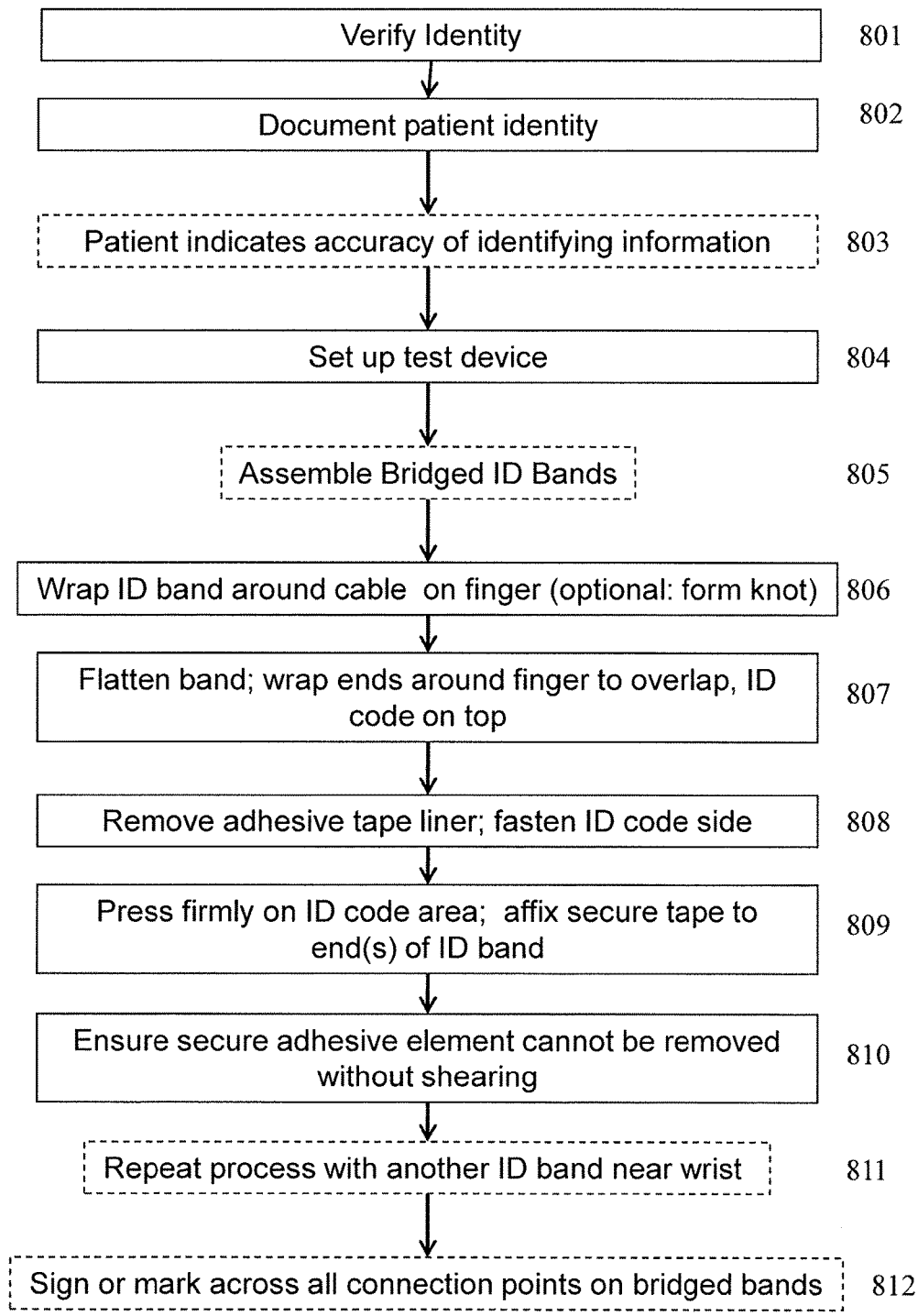
FIG. 8 illustrates a flowchart showing operation according to an alternate embodiment of the current design.

An alternative embodiment is shown in FIG. 8 and operates as follows. Initially, at box 801, appropriate personnel check the patient's identity, such as by using a driver's license to positively confirm identity. Box 802 represents documenting patient identity, such as on the test set-up form. Box 802 may also include documenting the type of ID band(s) being used, as well as serial number(s), size(e.g. pediatric size and/or adult sized), and the date of the test. In optional box 803, the patient may indicate, such as via signature or otherwise, that the information is accurate. Box 804 represents setting up the test device. As described, this may entail attaching the pulse-oximetry sensor on the patient's finger and placing the pulse-oximetry sensor signal cable along the back side of the wrist of the non-dominant arm of the patient/test subject. Box 805 further can include that the operator/therapist assembles a bridged unit that is made up of bands to be fitted around the patient's finger and wrist that are connected by a third band (see FIG. 4F). Additionally, if pre-assembled bridged units are available, box 805 may represent the procurement of a bridged unit. Box 806 further represents wrapping an ID band around the pulse-oximetry sensor signal cable near the finger, in an area where the patient would wear a ring, and optionally tying a simple but tight knot in the band with the serial number facing away from the patient. In place of a knot, the cable may be secured to the band with the adhesive section of the band, loops, snaps, or the like. Box 807 calls for flattening the band on both sides (with the serial code side away from wrist), and wrapping the two ends around the wrist so they overlap with the unique ID code on top. Box 808 indicates removing the adhesive tape liner, and fastening that ID code side securely to the other end. Box 809 indicates that the operator/therapist presses down firmly on the ID code area to ensure it cannot be pulled back off without shearing. Box 810 indicates that the operator/therapist ensures that the adhesive element cannot be removed with shearing the band or other evidence of tampering. Box 811, which is optional, indicates repeating the process with a second ID band on the patient's wrist. Box 812 further indicates that if the band around the patient's wrist and on the finger are bridged, the operator/therapist signs or marks across the bridging points such that tampering with the connections between finger and wrist bands at may be more evident. Subsequent to the foregoing, the test is performed.

Certain embodiments involve the use of passive securing methods, such as an identification band forming a knot, loop or other arrangement around the sensor and associated cable. In some embodiments, a cable associated with a sensor may be attached to an identification band with the adhesive section of the band or snaps. In further embodiments, the identification band may include an active component, such as employing wiring creating an electric circuit when the band is looped around the patient, and connected. The electric circuit design may be configured to monitor breaking of the electrical circuit to indicate tampering, such as monitoring voltage or current and recording when/if a reading goes to zero. Other forms of secure attachment to the patient may be employed.

Further, while several embodiments disclosed herein illustrate various loops used to attach the device to the patient, the present design is not limited in such attachment techniques. As described herein, multiple loops may be employed, as well as tapes, locking plastic arrangements or other materials that secure around the patient, Tyvek® (flashspun high-density polyethylene fiber material), other attachments, and so forth. And while some embodiments of the present device illustrates attachment around a wrist of a patient, other embodiments may attach to ankle/calf regions, neck, arm, around the head, or other appropriate locations on the patient depending on the needs of the test and requirements for securing. While sleep testing for apnea situations is disclosed in some embodiments, the present invention is not limited and may be used for other patient testing that may benefit from secure attachment to the patient.

In short, embodiments of the present design provide for tamper evident and tamper resistant ambulatory monitoring of a patient's oxygen saturation level, during the course of an overnight sleep study, and affords a high degree of control over the monitoring of signals generated from a pulse-oximetry sensor that advantageously positions and affixes the sensor and associated signal cable for reduced risk of fraud during test conduct. The system is thus configured to provide an identification band for fixing the signal cable to the patient's wrist or finger. A bridging identification band may be used to bridge two identification bands at the wrist and finger or two similarly adjacent locations on the body, such that the relative position of the two bands is maintained. A bridging identification band may additionally secure a sensor cable in place, such that tampering with the position of the sensor cable will be evident. The identification band material is able to retain markings from a pen, stamp, or like writing instrument. In addition, a tape configured to shred and/or tear when removed may be wrapped around the sensor and cable in combination with using the identification band(s).

Embodiments presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A system comprising:
   a first identification band comprising a first aperture;
   a second identification band comprising a second aperture, wherein the first and second identification bands show evidence of tampering upon removal, the evidence of tampering comprising shredding, tearing, discoloration, delamination, change in physical dimensions, or necking;
   a bridging band connected to the first and second identification bands; and
   a sensor signal cable passed through the second aperture of the second identification band, extended along the bridging band, passed through the first aperture of the first identification band to attach to an oxygen saturation sensor.

2. The system of claim 1, wherein the first identification band is configured to be placed around a finger of a patient and the second identification band is configured to be placed around a wrist of the patient.

3. The system of claim 1, wherein the first and second identification bands comprise serial numbers.

4. The system of claim 1, wherein the bridging band comprises serial numbers.

5. The system of claim 1, wherein the first identification band, the second identification band, and the bridging band are formed from a single piece of material.

6. A method comprising:
   attaching an oxygen saturation sensor with a sensor signal cable to a patient;
   forming a first loop in a first identification band to create a first aperture;
   forming a second loop in a second identification band to create a second aperture, the first and second identification bands show evidence of tampering upon removal, the evidence of tampering comprising shredding, tearing, discoloration, delamination, change in physical dimensions, or necking;
   connecting a bridging band to the first identification band and the second identification band;
   passing the sensor signal cable through at least one of the first aperture of the first identification band or the second aperture of the second identification band;
   extending the sensor signal cable along the bridging band; and
   attaching the sensor signal cable to the oxygen saturation sensor.

7. The method of claim 6, further comprising:
   connecting a PSG recording system input signal cable to the diagnostic monitoring test system; and
   encircling a connection formed where the sensor signal cable connects with the PSG recording system input signal cable with the first identification band or the second identification band.

8. The method of claim 6, further comprising:
   forming a third loop with the sensor signal cable; and
   passing at least one of the first identification band and the second identification band through the third loop.

* * * * *